US012635911B2

(12) United States Patent
Lee et al.

(10) Patent No.: US 12,635,911 B2
(45) Date of Patent: May 26, 2026

(54) ELECTRONIC DEVICE AND METHOD FOR CONTROLLING SAME

(71) Applicant: SAMSUNG ELECTRONICS CO., LTD., Suwon-si (KR)

(72) Inventors: Taehan Lee, Suwon-si (KR); Jungkeun Park, Suwon-si (KR); Seonghun Jeong, Suwon-si (KR); Jonghee Han, Suwon-si (KR); Kiyean Kim, Suwon-si (KR); Taeseon Kim, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 550 days.

(21) Appl. No.: 18/123,535

(22) Filed: Mar. 20, 2023

(65) Prior Publication Data

US 2023/0225637 A1    Jul. 20, 2023

Related U.S. Application Data

(63) Continuation of application No. PCT/KR2021/012599, filed on Sep. 15, 2021.

(30) Foreign Application Priority Data

Oct. 21, 2020    (KR) ........................ 10-2020-0136737

(51) Int. Cl.
| | |
|---|---|
| *A61B 5/12* | (2006.01) |
| *H04R 3/04* | (2006.01) |
| *H04R 29/00* | (2006.01) |

(52) U.S. Cl.
CPC .............. *A61B 5/125* (2013.01); *H04R 3/04* (2013.01); *H04R 29/001* (2013.01);
(Continued)

(58) Field of Classification Search
CPC ........... A61B 5/125; A61B 5/72; A61B 5/121; A61B 5/0002; A61B 5/6898; A61B 5/746;
(Continued)

(56) References Cited

U.S. PATENT DOCUMENTS

| | | |
|---|---|---|
| 5,601,091 A | 2/1997 | Dolphin |
| 9,497,530 B1 | 11/2016 | Campbell et al. |

(Continued)

FOREIGN PATENT DOCUMENTS

| | | |
|---|---|---|
| CN | 103892842 A | 7/2014 |
| CN | 104822119 A | 8/2015 |

(Continued)

OTHER PUBLICATIONS

International Search Report (PCT/ISA/210) issued by the International Searching Authority on Dec. 27, 2021 in corresponding International Application No. PCT/KR2021/012599.
(Continued)

*Primary Examiner* — Eric F Winakur
*Assistant Examiner* — Hy Khanh Doan
(74) *Attorney, Agent, or Firm* — Sughrue Mion, PLLC

(57) ABSTRACT

In some embodiments, the electronic device includes a speaker, a microphone, a memory, a digital signal processor (DSP), a driver, and a processor. The processor is configured to: obtain a first sound signal by combining a first signal, a second signal, and a first anti-phase signal; extract, from a second sound signal related to the first sound signal, a first DPOAE signal; obtain a third sound signal by combining a fourth signal, a fifth signal, and a second anti-phase signal; extract, from a fourth sound signal related to the third sound signal, a second DPOAE signal; obtain a user hearing profile based on the first and second DPOAE signals; and perform, based on the user hearing profile, at least one of a sound
(Continued)

volume change and an equalization (EQ) change of a sound to be output.

20 Claims, 15 Drawing Sheets

(52) U.S. Cl.
CPC .... *H04R 29/004* (2013.01); *A61B 2562/0204* (2013.01); *H04R 2430/01* (2013.01)

(58) Field of Classification Search
CPC .......... A61B 5/7475; A61B 2562/0204; H04R 29/001; H04R 29/004; H04R 2430/01; H04R 3/04; H04R 25/505; H04R 25/70
See application file for complete search history.

(56) References Cited

U.S. PATENT DOCUMENTS

| | | | |
|---|---|---|---|
| 2004/0234089 A1 | 11/2004 | Rembrand et al. | |
| 2007/0156063 A1 | 7/2007 | Zoth et al. | |
| 2011/0166806 A1 | 7/2011 | Choi | |
| 2015/0222999 A1 | 8/2015 | Rasmussen et al. | |
| 2017/0064434 A1 | 3/2017 | Campbell et al. | |
| 2017/0150908 A1 | 6/2017 | Nadon et al. | |
| 2017/0150909 A1 | 6/2017 | Dalhoff et al. | |
| 2017/0332977 A1 | 11/2017 | Dalhoff et al. | |
| 2017/0347181 A1 | 11/2017 | Campbell et al. | |
| 2019/0289409 A1* | 9/2019 | Greenberg | A61B 5/125 |
| 2020/0138340 A1 | 5/2020 | Nadon et al. | |
| 2020/0268288 A1 | 8/2020 | Dalhoff et al. | |

FOREIGN PATENT DOCUMENTS

| | | | |
|---|---|---|---|
| CN | 107582068 A | 1/2018 | |
| JP | 2002-503972 A | 2/2002 | |
| KR | 10-2007-0099749 A | 10/2007 | |
| KR | 10-2010-0066749 A | 6/2010 | |
| KR | 10-2011-0008505 A | 1/2011 | |
| KR | 10-2011-0080595 A | 7/2011 | |
| KR | 10-2012-0091698 A | 8/2012 | |
| KR | 10-1535112 B1 | 7/2015 | |
| KR | 10-1712099 B1 | 3/2017 | |

OTHER PUBLICATIONS

Written Opinion (PCT/ISA/237) issued by the International Searching Authority on Dec. 27, 2021 in corresponding International Application No. PCT/KR2021/012599.

Wei-Chen Hsiao et al., "Measuring Distortion-Product Otoacoustic Emission With a Single Loudspeaker in the Ear: Stimulus Design and Signal Processing Techniques", Frontiers in digital health, vol. 3, 13 pages, Sep. 1, 2021, doi: 10.3389/fdgth.2021.724539.

European Extended Search Report issued Dec. 14, 2023 issued by the European Patent Office for EP Patent Application No. 21883025.5.

Communication dated Jan. 27, 2026, issued by the China National Intellectual Property Administration in Chinese Application No. 202180072310.2.

Borges et al., "An Adaptive Occlusion Canceller for Hearing Aids", 21st European Signal Processing Conference (EUSIPCO 2013), pp. 1-5 (5 pages total).

Communication dated Feb. 3, 2026, issued by the Korean Ministry of Intellectual Property in Korean Application No. 10-2020-0136737.

* cited by examiner

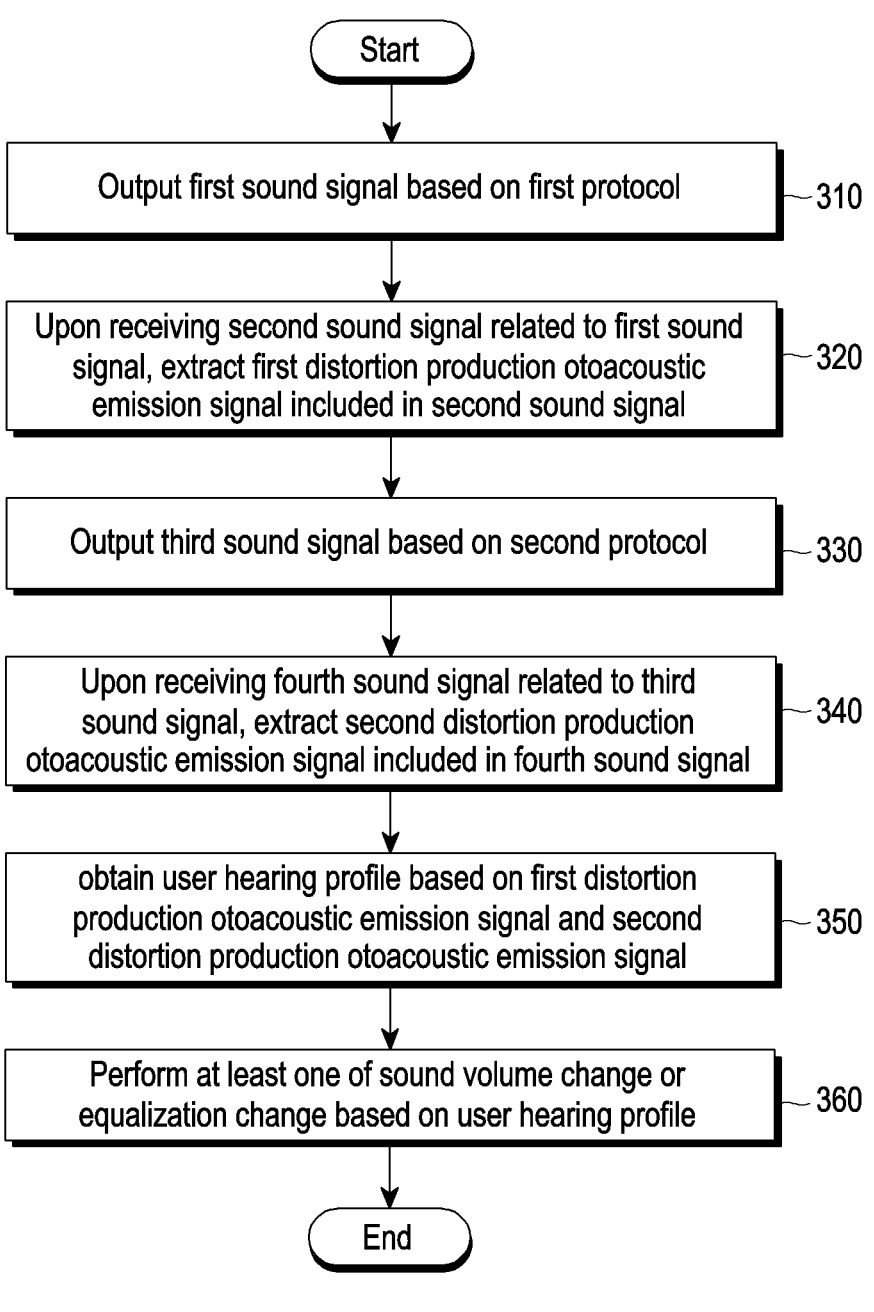

Start

Output first sound signal based on first protocol ~310

Upon receiving second sound signal related to first sound signal, extract first distortion production otoacoustic emission signal included in second sound signal ~320

Output third sound signal based on second protocol ~330

Upon receiving fourth sound signal related to third sound signal, extract second distortion production otoacoustic emission signal included in fourth sound signal ~340 obtain user hearing profile based on first distortion production otoacoustic emission signal and second distortion production otoacoustic emission signal ~350

Perform at least one of sound volume change or equalization change based on user hearing profile ~360

End

FIG. 3

$410 \sim f_1$ $411 \sim f_2$ $420 \sim 2f_1 - f_2$
(Anti-phase)

150

First
sound signal

10

Second
sound signal

160

$f_2 - f_1$          $f_1$          $f_2$          $2f_2 - f_1$

412

—— $2f_1 - f_2$ (Inter-modulation distortion)

- - - - $2f_1 - f_2$ (Anti-phase) $\sim 420$

DPOAE $f_2 - f_1$     $2f_1 - f_2$     $f_1$          $f_2$     $2f_2 - f_1$

430

510

$f_1$ $f_2$

520

$f_1$ $f_2$

521 — $2f_1 - f_2$(Predistortion)

20

2CC Coupler
(No Ear)

530     540

SNR (dB)  10

5

0

ELECTRONIC DEVICE AND METHOD FOR CONTROLLING SAME

CROSS-REFERENCE TO RELATED APPLICATIONS

This application is a continuation application of International Application No. PCT/KR2021/012599, filed on Sep. 15, 2021, which claims priority to Korean Patent Application 10-2020-0136737, filed on Oct. 21, 2020, in the Korean Intellectual Property Office, the disclosures of which are incorporated by reference herein in their entireties.

BACKGROUND

1. Field

The present disclosure relates generally to signal processing, and more particularly, to an electronic device for a hearing test using distortion production otoacoustic emissions and a control method thereof.

2. Description of Related Art

As technology advances, related services and functions are being provided through related electronic devices (e.g., smartphones, or other portable electronic devices). As a result, due to increases in the use of personal listening devices, a growing number of users may experience hearing loss.

Accordingly, manufacturers of related electronic devices may have more of an interest in the area of personal hearing test and care on an electronic device.

Related hearing tests may include, but not be limited to, pure tone audiometry (PTA), transient evoked otoacoustic emissions (TEOAEs), and distortion production otoacoustic emissions.

A PTA may refer to a manual test performed by letting the user listen to pure tones generated in an anechoic chamber and press a button. A PTA test may have a benefit in that the test may allow for testing on various auditory organs. However, the PTA test may have a drawback in that the test may need a long term test, when compared to other related hearing tests.

In a transient evoked otoacoustic emissions test, a sound having a wide frequency range may be momentarily output through a speaker, and the responding sound may be received through a microphone with a delay. This test may check for the condition of hair cells for each frequency based on the response characteristics over time. The transient evoked otoacoustic emissions test may be performed on each ear using one speaker. However, the speaker may be vulnerable to ambient noise and, as a result, the test may have poor accuracy.

The distortion production otoacoustic emissions test may output two pure signals having the frequencies of f1 and f2 for both ears, respectively, may receive the responding sound through a microphone, and may test hearing based on a third-order low-frequency inter-modulation distorted signal (e.g., having a frequency of 2f1−f2) which, while not outputted by the test equipment, may be included in the responding sound. As a result, the distortion production otoacoustic emissions test may have the advantages of having a high accuracy and being resistant to noise, when compared to other related hearing tests.

While the distortion production otoacoustic emissions test may be advantageous for early detection of hearing loss, the test may require two speakers for each ear, respectively, to prevent unwanted distorted signals. That is, since two speakers must operate separately in one listening device corresponding to one ear, two sound processors and two drivers for channel control may be needed for each ear. Moreover, in order to test on both ears at the same time, two sound processors and two drivers may be needed for each ear (e.g., four sound processors and four drivers in total), which may pose limitations on the hardware needed for performing a hearing test using distortion production otoacoustic emissions.

Thus, there exists a need for further improvements in performing hearing tests, as the need for using distortion production otoacoustic emissions may be constrained by the hardware needed to perform the hearing test. Improvements are presented herein. These improvements may also be applicable to other multi-audio signal processing technologies and to the standards that employ these technologies.

SUMMARY

According to various aspects of the present disclosure, there are provided electronic devices capable of performing a distortion production otoacoustic emissions-based hearing test even with a single speaker operating on a channel for each ear by combining a sound signal for test and an anti-phase signal for canceling off the distorted signal related to the distortion production otoacoustic emissions and a control method thereof.

According to an aspect of the present disclosure, an electronic device is provided. The electronic device includes a speaker, a microphone, a memory storing instructions and a plurality of protocols, a digital signal processor (DSP), a driver, and a processor operatively coupled with the speaker, the microphone, the memory, the DSP, and the driver. The driver is configured to convert a digital signal output from the DSP into an analog signal and output the analog signal to the speaker. The processor is configured to execute the instructions to control the DSP to obtain a first sound signal by combining a first signal, a second signal, and a first anti-phase signal, based on a first protocol from among the plurality of protocols. The first anti-phase signal has a third frequency related to a distortion production otoacoustic emission (DPOAE) of a first frequency of the first signal and a second frequency of the second signal. The processor is further configured to control the driver to output, through the speaker, the first sound signal. The processor is further configured to receive, through the microphone, a second sound signal related to the first sound signal, in response to the output of the first sound signal. The processor is further configured to extract, from the second sound signal, a first DPOAE signal of the third frequency. The processor is further configured to control the DSP to obtain a third sound signal by combining a fourth signal, a fifth signal, and a second anti-phase signal, based on a second protocol among the plurality of protocols. The second anti-phase signal having a sixth frequency related to a DPOAE of a fourth frequency of the fourth signal and a fifth frequency of the fifth signal. The processor is further configured to control the driver to output, through the speaker, the third sound signal. The processor is further configured to receive, through the microphone, a fourth sound signal related to the third sound signal, in response to the output of the third sound signal. The processor is further configured to extract, from the fourth sound signal, a second DPOAE signal of the sixth frequency. The processor is further configured to obtain a user hearing profile based on the first DPOAE signal and the second DPOAE signal. The processor is further configured to perform, based on the user hearing profile, at least one of a sound volume change and an equalization (EQ) change of a sound to be output.

According to an aspect of the present disclosure, a method for controlling an electronic device is provided. The method includes outputting, through a speaker of the electronic device, a first sound signal obtained by combining a first signal having a first frequency, a second signal having a second frequency, and a first anti-phase signal having a third frequency related to a DPOAE of the first frequency and the second frequency, based on a first protocol from among a plurality of protocols stored in a memory of the electronic device. The method further includes, in response to receiving, through a microphone of the electronic device, a second sound signal related to the first sound signal, extracting, from the second sound signal, a first DPOAE signal of the third frequency. The method further includes outputting, through the speaker, a third sound signal obtained by combining a fourth signal having a fourth frequency, a fifth signal having a fifth frequency, and a second anti-phase signal having a sixth frequency related to a DPOAE of the fourth frequency and the fifth frequency, based on a second protocol from among the plurality of protocols. The method further includes, in response to receiving, through the microphone, a fourth sound signal related to the third sound signal, extracting, from the fourth sound signal, a second DPOAE signal of the sixth frequency. The method further includes obtaining a user hearing profile based on the first DPOAE signal and the second DPOAE signal. The method further includes performing, based on the user hearing profile, at least one of a sound volume change and an EQ change of a sound to be output.

According to an aspect of the present disclosure, an electronic device is provided. The electronic device includes a memory storing instructions, and a processor operatively coupled with the memory. The processor is configured to execute the instructions to extract a plurality of DPOAE signals from a corresponding plurality of received sound signals. The corresponding plurality of received sound signals have been received in response to transmitting a plurality of related sound signals that have been obtained by combining, according to respective protocols of a plurality of protocols, a first signal, a second signal, and an anti-phase signal. The anti-phase signal has a third frequency related to a DPOAE of a first frequency of the first signal and a second frequency of the second signal. The processor is further configured to obtain a user hearing profile based on the plurality of DPOAE signals. The processor is further configured to perform, based on the user hearing profile, at least one of a sound volume change and an EQ change of a sound to be output.

According to various aspects of the disclosure, it may be possible to perform a hearing test using distortion production otoacoustic emissions using only one speaker having one channel for each ear.

According to various aspects of the disclosure, it may be possible to reduce a user's hearing loss by obtaining equalization customized for each user to fit the user's hearing condition and outputting a sound signal.

Additional aspects will be set forth in part in the description which follows and, in part, will be apparent from the description, or may be learned by practice of the presented embodiments.

BRIEF DESCRIPTION OF THE DRAWINGS

The above and other aspects, features, and advantages of certain embodiments of the present disclosure will be more apparent from the following description taken in conjunction with the accompanying drawings, in which:

FIG. 3 is a view illustrating a method for controlling an electronic device using distortion production otoacoustic emissions, according to an embodiment of the disclosure;

DETAILED DESCRIPTION

The following description with reference to the accompanying drawings is provided to assist in a comprehensive understanding of embodiments of the present disclosure defined by the claims and their equivalents. Various specific details are included to assist in understanding, but these details are considered to be exemplary only. Therefore, those of ordinary skill in the art will recognize that various changes and modifications of the embodiments described herein can be made without departing from the scope and spirit of the disclosure. In addition, descriptions of well-known functions and structures are omitted for clarity and conciseness.

Reference throughout the present disclosure to "one embodiment," "an embodiment," "an example embodiment," or similar language may indicate that a particular feature, structure, or characteristic described in connection with the indicated embodiment is included in at least one embodiment of the present solution. Thus, the phrases "in one embodiment", "in an embodiment," "in an example embodiment," and similar language throughout this disclosure may, but do not necessarily, all refer to the same embodiment.

It is to be understood that the specific order or hierarchy of blocks in the processes/flowcharts disclosed are an illustration of exemplary approaches. Based upon design preferences, it is understood that the specific order or hierarchy of blocks in the processes/flowcharts may be rearranged. Further, some blocks may be combined or omitted. The accompanying claims present elements of the various blocks in a sample order, and are not meant to be limited to the specific order or hierarchy presented.

Hereinafter, various embodiments of the present disclosure are described with reference to the accompanying drawings.

Figure 1:
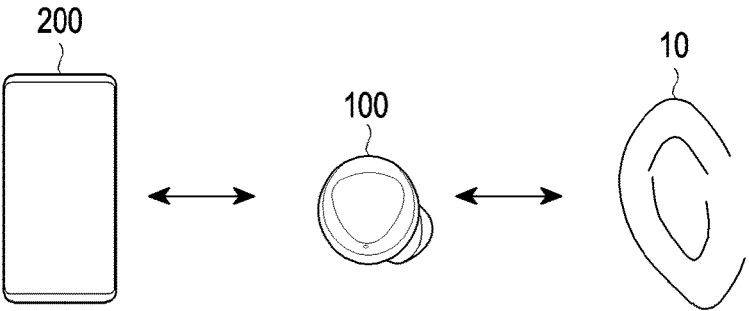
FIG. 1 is a view illustrating a hearing test system using distortion production otoacoustic emissions, according to an embodiment of the disclosure.

FIG. 1 illustrates a hearing test system using distortion production otoacoustic emissions (DPOAEs), according to an embodiment.

According to an embodiment, the hearing test system may include an electronic device 100. The electronic device 100 may output a sound and then receive a sound generated from an ear of the user 10.

According to an embodiment, the electronic device 100 may determine whether the hearing of the user 10 is normal based on a distortion production otoacoustic emission signal from among the sounds generated from the ear of the user 10, according to the output of the sound. For example, the electronic device 100 may output a single sound signal which is a combination of a plurality of signals having different frequencies through a single speaker 150. The plurality of signals having the different frequencies may include a pure tone signal of a first frequency, a pure tone signal of a second frequency, a plurality of inter-modulation distorted signals related to the pure tone signal of the first frequency and the pure tone signal of the second frequency, and an anti-phase signal of the distortion production otoacoustic emission frequency among the plurality of inter-modulation distorted signals. An operation of combining the plurality of signals is described below with reference to FIG. 4A.

The inter-modulation distortion may refer distortion caused as two independent input signals are combined in a filter. That is, the inter-modulation distortion may refer to non-linear distortion by which the frequencies generated by linear combination of the fundamental frequency of the input signal and the harmonics are included in the output signal. For example, when a first signal with a first frequency (e.g., f1) and a second signal with a second frequency (e.g., f2) are combined, a plurality of inter-modulation distorted signals may be generated, such as, but not limited to, signals with frequencies of f2−f1, 2f1−f2, and 2f2−f1.

Otoacoustic emissions may refer to sound energy generated spontaneously and/or amplified by sound stimulation in the outer hair cells of the cochlea. That is, otoacoustic emissions may occur regardless of whether the auditory nerve is severed or not. Alternatively or additionally, otoacoustic emissions may not appear when insensitive to changes in external conditions and/or in cochlear hearing loss. Otoacoustic emissions may allow for checking on (e.g., testing for) abnormalities in the cochlea and/or auditory hair cells within a relatively short time in a simplified manner without harming the auditory function. Consequently, otoacoustic emissions may be used as to obtain an early diagnosis of hearing loss and for objective tests, such as, but not limited to, hearing tests for newborns and children.

Distortion production otoacoustic emissions may be a type of otoacoustic emissions. Distortion production otoacoustic emissions may refer to otoacoustic emissions of various frequencies that may occur at the overlapping part of two pure tone stimulating sounds having two different frequencies (e.g., first signal f1, second signal f2) that have been applied simultaneously. That is, the distortion production otoacoustic emissions may be a product (e.g., a result) of the non-linear distortion caused by the cochlea. The reaction size of the distortion production otoacoustic emissions may be affected by the relative and/or absolute strengths of the pure tones and the frequency ratio of the pure tones. For example, when the frequency ratio is 1.2 (e.g., f2=1.2×f1) and the strength of the first signal f1 is higher (e.g., greater) than the strength of the second signal f2 by approximately 5 to 10 decibel of sound pressure level (dB SPL), a strong reaction (e.g., distortion) may occur at a frequency between 2f1 and f2.

In an embodiment, the electronic device 100 may repeat the operation of adjusting the frequency of the sound and outputting the adjusted sound. Alternatively or additionally, the electronic device 100 may repeat the operation of receiving the distortion production otoacoustic emission for the (adjusted) output sound. That is, the electronic device 100 may obtain the user's hearing profile based on the plurality of distortion production otoacoustic emission signals received.

According to various embodiments, the electronic device 100 may include an ear probe and output the sound with the ear probe partially inserted in the outer ear of the user 10.

According to various embodiments, the ear probe of the electronic device 100 may not only be inserted into the outer ear of the user 10, but also may be wrapped around a part of the ear of the user 10 from the outside. That is, at least one portion of the electronic device 100 may be disposed inserted in the outer ear and at least another portion of the electronic device 100 may be disposed around the outside of the ear.

According to an embodiment, the hearing test system may further include an external device 200 communicating with the electronic device 100. The electronic device 100 may output the stored sound and/or may receive a sound signal from the external device 200 and output the obtained sound. As shown in FIG. 1, the electronic device 100 and the external device 200 may communicate wirelessly, but the present disclosure is not limited in this regard. For example, the electronic device 100 and the external device 200 may communicate with each other wiredly, wirelessly, or a combination thereof.

As shown in FIG. 1, the external device 200 may be in the form of a smart phone in FIG. 1. However, the present disclosure is not limited in this regard. For example, the external device 200 may include any device capable of communicating with the electronic device 100, such as, but not limited to, a desktop personal computer (PC), a television (TV), a compact disc (CD) player, a Moving Picture Experts Group Phase 1 (MPEG-1) Audio Layer III (MP3) player, or a server.

Continuing to refer to FIG. 1, one earphone may be worn on one ear of the user 10 as the electronic device 100. However, the present disclosure is not limited in this regard. For example, a plurality of electronic devices 100 may be worn on both ears of the user 10, respectively.

Figure 2:
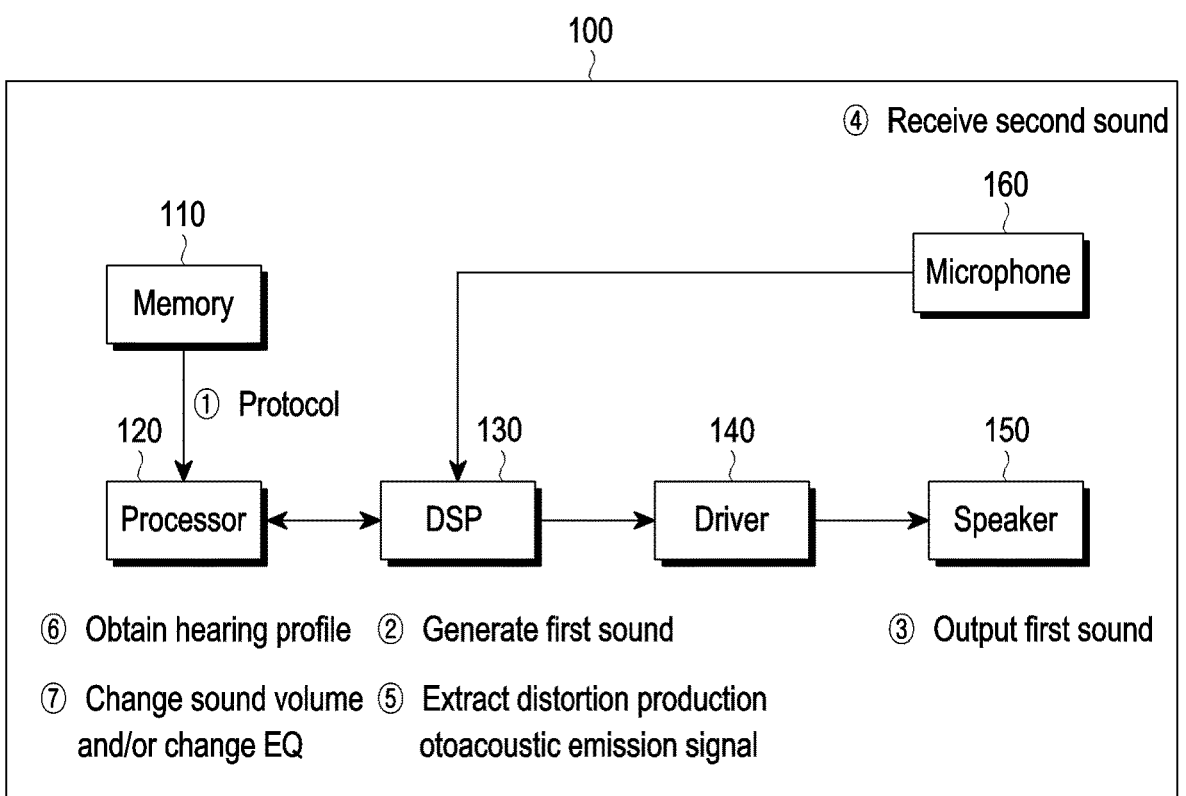
FIG. 2 is a view illustrating a configuration and operations of an electronic device, according to an embodiment of the disclosure.

FIG. 2 illustrates an electronic device 100, according to an embodiment. The electronic device 100 in FIG. 2 may be one of a plurality of earphones worn on the user's both ears.

According to an embodiment, the electronic device 100 may include a memory 110, a processor 120, a digital signal processor (DSP) 130, a driver 140, a speaker 150, and a microphone 160.

According to an embodiment, a plurality of protocols for a hearing test may be stored in the memory 110. The protocol may include information about two different frequencies (e.g., f1 and f2) for a hearing test in a specific frequency range and information about the anti-phase signal of the distortion production otoacoustic emission frequency of a plurality of inter-modulation distorted signals caused by a combination of the signals of the two different frequencies. For example, the distortion production otoacoustic emission frequency may be 2f1−f2 as the frequency of the third-order low-frequency inter-modulation distortion. According to an embodiment, the frequency ranges to be measured by the plurality of protocols, respectively, may at least partially differ.

According to an embodiment, the processor 120 may execute software (e.g., a program) to control at least one other component (e.g., a hardware or software component) of the electronic device 100 connected with the processor 120 and may process and/or compute various data. According to one embodiment, as at least part of the data processing or computation, the processor 120 may store a command and/or data received from another component (e.g., sensor module or communication module, not shown) and store the result data in the memory 110.

According to an embodiment, the processor 120 may obtain (①) at least one protocol from the memory 110 and may control the DSP 130 to generate (②) a first sound based on one of the obtained at least one protocol.

According to an embodiment, the DSP 130 may process digital signals under the control of the processor 120. For example, the DSP 130 may output the first sound signal through one channel per speaker 150 corresponding to one ear of the user. The first sound signal may be a sound signal for detecting distortion production otoacoustic emission.

For example, the DSP 130 may combine the two signals having different frequencies and the signal for canceling off the inter-modulation distorted signal having the same frequency as the distortion production otoacoustic emission generated due to the combination of the two signals based on the protocol for the hearing test and output the combined signal to the driver 140. The operation of combining the signals is described below with reference to FIG. 4A. Thus, it may be possible to perform a hearing test based on distortion production otoacoustic emissions using only one speaker 150 for each ear.

According to an embodiment, the driver 140 may convert the digital signal received from the DSP 130 into an analog signal and output the analog signal to the speaker 150.

According to an embodiment, the speaker 150 may output (③) the first sound signal to the outside of the electronic device 100. For example, the speaker 150 may be disposed on a part of the ear probe of the electronic device 100 to output the first sound signal.

According to an embodiment, the microphone 160 may receive an external sound signal of the electronic device 100. The microphone 160 may receive the analog signal and convert it into a digital signal, and transfer the converted digital signal to the DSP 130.

For example, the microphone 160 may be disposed on a part of the ear probe of the electronic device 100 and, after the first sound signal is output through the speaker 150, the microphone 160 may receive (④) a second sound signal related to the output first sound signal. For example, a distortion production otoacoustic emission signal generated in the cochlea of the user due to the output first sound signal may be included in the second sound signal related to the output first sound signal.

According to an embodiment, the DSP 130 may extract (⑤) the distortion production otoacoustic emission signal from the second sound signal received through the microphone 160. For example, the frequency of the distortion production otoacoustic emission signal may be 2f1−f2 based on the frequencies f1 and f2 of the two pure tone signals included in the first sound signal.

According to various embodiments, the second sound signal received through the microphone 160 may be transferred to the processor 120. The operation of extracting the distortion production otoacoustic emission signal from the second sound signal may be performed by the processor 120.

According to various embodiments, the processor 120 may measure external noise through the microphone 160 and determine whether to perform a hearing test based on the external noise measurement results.

According to an embodiment, the processor 120 may obtain (⑥) the user's hearing profile based on the extracted distortion production otoacoustic emission signal. For example, the processor 120 may determine whether the user's hearing is normal in a specific frequency range based on the strength of the extracted distortion production otoacoustic emission signal relative to the strength of the first frequency signal and the strength of the second frequency signal included in the output first sound signal.

According to an embodiment, the processor 120 may change protocols and repeat the operation of outputting the sound signal for a hearing test and the operation of extracting the distortion production otoacoustic emission signal. Thus, the processor 120 may obtain the user's hearing profile in a plurality of frequency ranges based on a plurality of distortion production otoacoustic emission signals.

According to an embodiment, the processor 120 may perform (⑦) sound volume change and/or equalization (EQ) change based on the obtained user hearing profile. For example, upon determining that the user's hearing is deteriorated based on the user hearing profile, the processor 120 may control the speaker 150 to reduce the volume of the output sound signal.

In an optional or additional embodiment, the processor 120 may change the equalization based on the user's hearing profile. Equalization may refer to partially adjusting the sound signal from a low pitch to a high pitch, according to the music genre or the user's taste. For example, the processor 120 may change the equalization so that the difference in strength (e.g., volume) between the plurality of frequencies included in the sound signal to be output falls within a set range based on the user's hearing profile.

For example, the processor 120 may change the equalization to reduce the volume of a specific frequency signal in the sound signal based on the user's hearing profile.

According to various embodiments, when the user's personal equalization is pre-stored, the processor 120 may update the user's hearing profile with the pre-stored equalization. According to an optional or additional embodiment, when the user's personal equalization is absent, the processor 120 may store the equalization changed based on the user's hearing profile.

Thus, it may be possible to obtain equalization customized for each user to fit the user's hearing condition.

According to various embodiments, upon determining that the user's hearing is deteriorated based on the user's hearing profile, the processor 120 may provide feedback to notify the user that their hearing is deteriorated. For example, upon determining that the user's hearing is deteriorated, the processor 120 may display a message indicating the deterioration of hearing on the display of the electronic device 100 and/or may transmit another message to an external device 200 and cause the external device 200 to display the another message on the display of the external device 200. In an embodiment, upon determining that the user's hearing is deteriorated, the processor 120 may output a notification of the deterioration of hearing through the speaker 150.

According to various embodiments, although not shown in FIG. 2, the electronic device 100 may further include at least one of a communication module, a sensor, or a power supply unit.

FIG. 3 is a flowchart illustrating a method for controlling an electronic device 100 using distortion production otoacoustic emissions, according to an embodiment.

According to an embodiment, in operation 310, the electronic device 100 (e.g., the processor 120 and/or the DSP 130) may output a first sound signal based on a first protocol. For example, the electronic device 100 may output, through the speaker 150, a first sound signal obtained by combining a plurality of signals using the first protocol among a plurality of protocols stored in the memory 110. According to an embodiment, the electronic device 100 may output the first sound signal through the speaker 150 corresponding to one ear using one channel.

Figure 4A:
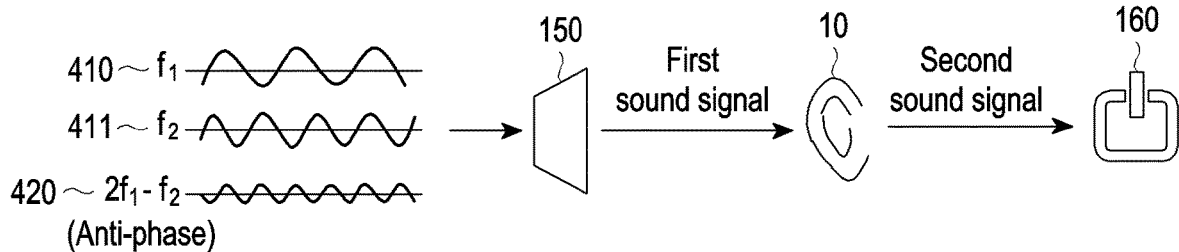
FIG. 4A is a view illustrating a configuration and operations of an electronic device, according to an embodiment of the disclosure.

For example, as shown in FIG. 4A, the electronic device 100 may output, through the speaker 150, the first sound signal which is a combination of a first signal 410 with a frequency of f1, a second signal 411 with a frequency of f2, and an anti-phase signal 420 with a frequency of 2f1–f2, which is a frequency related to the distortion production otoacoustic emission of f1 and f2.

According to an embodiment, combining two signals to output signals of two different frequencies through one channel may cause a plurality of inter-modulation distorted signals. For example, if the first signal 410 and the second signal 411, then a plurality of inter-modulation distorted signals may be generated, such as, but not limited to, signals with frequencies of f2–f1, 2f1–f2, and 2f2–f1.

Figure 4B:
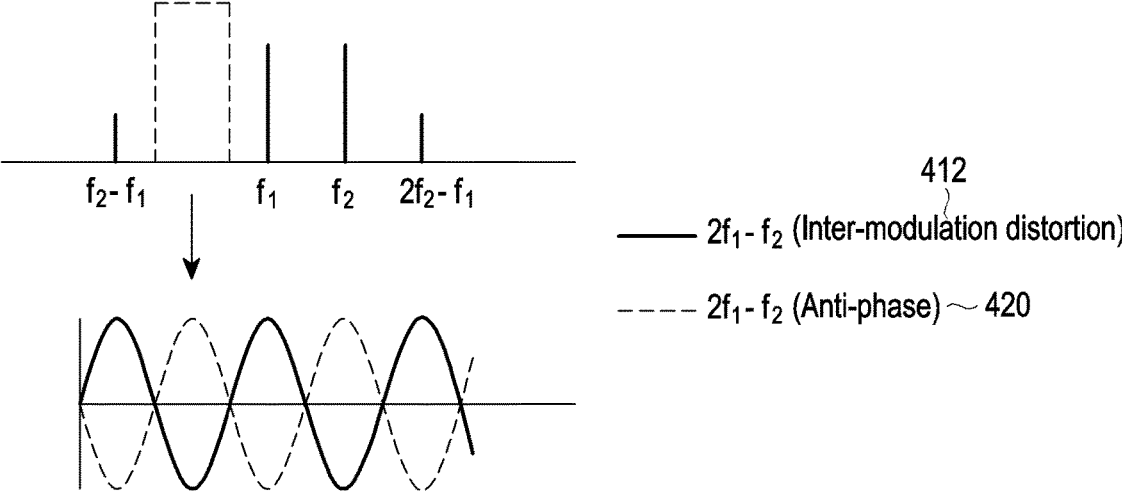
FIG. 4B is a view illustrating a sound signal output from a speaker, according to an embodiment of the disclosure.

According to an embodiment, as shown in FIG. 4B, the electronic device 100 may output, through the speaker 150, the first sound signal in which the inter-modulation distorted signal with the frequency of 2f1–f2 has been canceled out from among the plurality of inter-modulation distorted signals of f1 and f2. For example, the inter-modulation distorted signal with the frequency of 2f1–f2 may have been canceled out by further combining the first sound signal with the anti-phase signal 420 of the inter-modulation distorted signal 412 with the frequency of 2f1–f2, which is the frequency related to the distortion production otoacoustic emission of f1 and f2 from among the plurality of inter-modulation distorted signals.

Referring to FIG. 3, according to an embodiment, in operation 320, upon receiving the second sound signal related to the first sound signal, the electronic device 100 may extract the first distortion production otoacoustic emission signal included in the second sound signal.

Figure 4C:
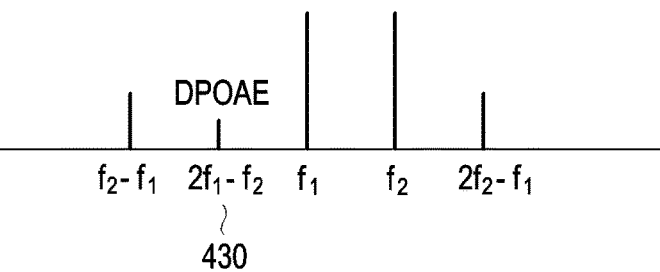
FIG. 4C is a view illustrating a sound signal input from a user's ear, according to an embodiment of the disclosure.

For example, referring to FIG. 4A, the electronic device 100 may output the first sound signal through the speaker 150 and then receive the second sound signal through the microphone 160. For example, as shown in FIG. 4C, the second sound signal received through the microphone 160 after the first sound signal is output may include a distortion production otoacoustic emission (DPOAE) signal 430 generated from the ear of the user 10, and the electronic device 100 may extract the DPOAE signal 430 from the second sound signal. For that reason, as shown in FIG. 4B, the first sound signal that is output is a signal in which the inter-modulation distorted signal 412 with a frequency of 2f1–f2 has been canceled out from among the plurality of inter-modulation distorted signals of f1 and f2. As a result, the distortion production otoacoustic emission signal 430 generated from the cochlea of the user 10, stimulated by the pure tone signals whose frequencies are f1 and f2, may be precisely extracted.

According to an embodiment, in operation 330, the electronic device 100 may output a third sound signal based on a second protocol. For example, the electronic device 100 may output, through the speaker 150, a third sound signal obtained by combining a plurality of signals using the second protocol from among a plurality of protocols stored in the memory 110. According to an embodiment, the electronic device 100 may output the third sound signal through the speaker 150 corresponding to one ear using one channel.

According to an embodiment, the electronic device 100 may output, through the speaker 150, the third sound signal which may be a combination of a pure tone signal with a frequency of f3, a pure tone signal with a frequency of f4, and an anti-phase signal of 2f3–f4, which is a frequency related to the distortion production otoacoustic emission of f3 and f4.

According to an embodiment, in operation 340, upon receiving the fourth sound signal related to the third sound signal, the electronic device 100 may extract the second distortion production otoacoustic emission signal included in the fourth sound signal. For example, the electronic device 100 may output the third sound signal through the speaker 150 and then receive the fourth sound signal through the microphone 160. The fourth sound signal received through the microphone 160 after the third sound signal is output may include the distortion production otoacoustic emission signal generated from the cochlea of the user 10 stimulated by the pure tone signal with the frequency of f3 and the pure tone signal with the frequency of f4. The electronic device 100 may extract the distortion production otoacoustic emission signal from the fourth sound signal.

According to an embodiment, the electronic device 100 may repeat the operation of outputting the sound signal whose frequency is changed and the operation of extracting the distortion production otoacoustic emission signal for the output sound based on the plurality of protocols. That is, for each protocol of the plurality of protocols, the electronic device 100 may perform the operation of outputting the sound signal corresponding to that protocol and perform the operation of extracting the distortion production otoacoustic emission signal for the output sound corresponding to that protocol.

According to an embodiment, in operation 350, the electronic device 100 may obtain the user's hearing profile based on the first distortion production otoacoustic emission signal and the second distortion production otoacoustic emission signal. For example, the electronic device 100 may obtain the user's hearing profile in a plurality of frequency ranges based on a plurality of distortion production otoacoustic emission signals.

According to an embodiment, in operation 360, the electronic device 100 may perform at least one of sound volume change or equalization change based on the user's hearing profile. For example, upon determining that the user's hearing is deteriorated based on the user hearing profile, the electronic device 100 may control the speaker 150 to reduce the volume of the output sound signal and/or change the equalization of the output sound signal to reduce the volume of a specific frequency signal.

According to various embodiments, when the user's personal equalization is pre-stored, the electronic device 100 may update the user's hearing profile with the pre-stored equalization. For example, the user's personal equalization may be stored in the memory 110 of the electronic device 100 or received from an external device 200 through the communication module.

According to an optional or additional embodiment, when the user's personal equalization is absent, the electronic device 100 may store the equalization changed based on the user's hearing profile.

According to another optional or additional embodiment, upon determining that the user's hearing is deteriorated based on the user's hearing profile, the electronic device 100 may provide a message to notify the user that her hearing is deteriorated.

Figure 5A:
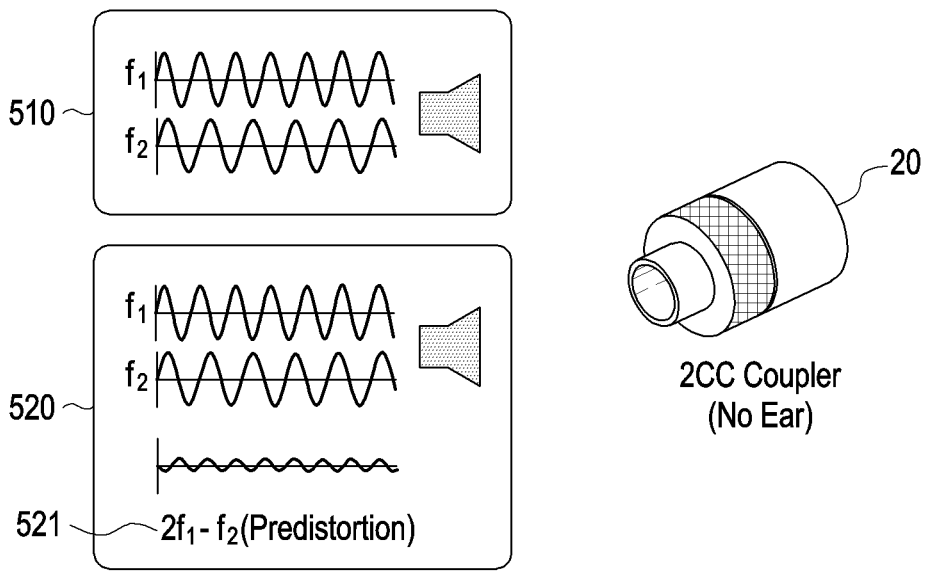
FIGS. 5A and 5B are views illustrating a sound signal output from a speaker, according to an embodiment of the disclosure.
Figure 5B:
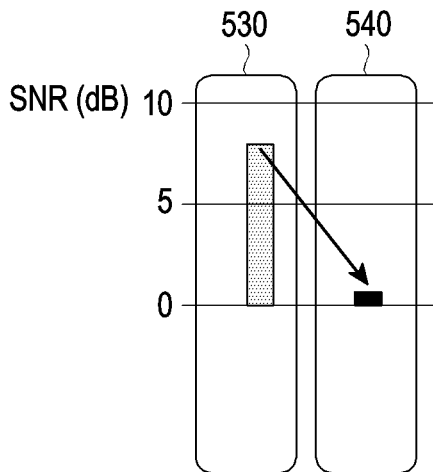

FIGS. 5A and 5B are views illustrating a sound signal output from a speaker 150, according to an embodiment of the disclosure.

For example, the electronic device 100 may output a sound signal to a two (2) cubic centimeter (e.g., 2 cc) coupler 20. The 2 cc coupler 20 may be a component used for performance analysis of a hearing aid. For example, the 2 cc coupler 20 may have a two (2) cc shape similar to the volume of the user's ear canal. Although a 2 cc coupler 20 is shown in FIG. 5A, a coupler 20 having a volume other than 2 cc may be used depending on the volume of the user's ear canal. That is, the present disclosure is not limited in this regard. For example, other couplers having other volumes and/or shapes may be used without deviating from the scope of the present disclosure.

While a typical human ear may not have a linear characteristic, the 2 cc coupler 20 may have a linear characteristic. The linear characteristic of the 2 cc coupler 20 may refer to a sound signal having a plurality of frequencies is output to the 2 cc coupler 20, no inter-modulation distorted sound for a plurality of frequencies may be included in the reflection signal of the output sound signal. That is, no inter-modulation distorted sound may be generated for the sound signal having a plurality of frequencies through the 2 cc coupler 20.

Referring to FIG. 5A, the electronic device 100 may output, to the 2 cc coupler 20 through the speaker 150, each of the sound signal 510 may be obtained by combining a first signal with a frequency of f1 and a second signal with a frequency of f2, and a sound signal 520 may be obtained by combining a first signal with a frequency of f1, a second signal with a frequency of f2, and an anti-phase signal 521 with a frequency of 2f1−f2, which is a frequency related to the distortion production otoacoustic emission of f1 and f2.

Further, as shown in FIG. 5B, the electronic device 100 may measure the strength of the signal of the frequency (e.g., third-order low frequency inter-modulation distortion) related to the distortion production otoacoustic emission included in the reflection signal obtained from the 2 cc coupler 20.

Referring to FIG. 5B, the strength (e.g., signal-to-noise ratio (SNR)) of the signal 530 with the frequency related to the distortion production otoacoustic emission that is included in the reflection signal of the sound signal 510 obtained by combining the first signal with a frequency of f1 and the second signal with a frequency of f2, may be approximately 7 dBSPL, for example.

However, the strength of the signal 540 with the frequency related to the distortion production otoacoustic emission that is included in the reflection signal of the sound signal 520 obtained by combining the first signal with a frequency of f1, the second signal with a frequency of f2, and the anti-phase signal 521 with a frequency of 2f1−f2 which is the frequency related to the distortion production otoacoustic emission of f1 and f2, may be approximately 1 dBSPL.

Thus, it may be identified that the signal with the frequency related to distortion production otoacoustic emission may be canceled (or significantly reduced) in the sound signal output through the speaker 150 using destructive interference by combining the anti-phase signal with a frequency of 2f1−f2, which is the frequency related to the distortion production otoacoustic emission of f1 and f2.

Figures 6A, 6B:
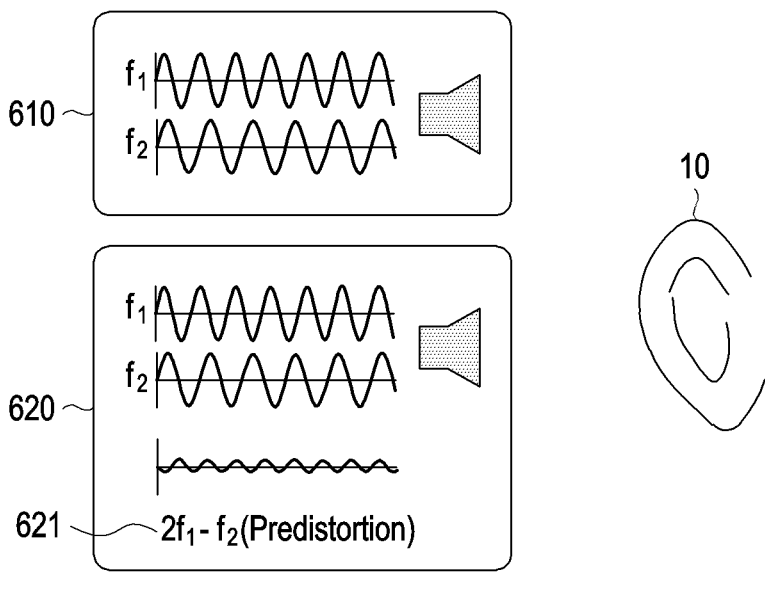
FIGS. 6A and 6B are views illustrating a sound signal input from a user's ear, according to an embodiment of the disclosure.

FIGS. 6A and 6B are views illustrating a sound signal input from a user's ear, according to an embodiment of the disclosure.

For example, the electronic device 100 of the disclosure may output a sound signal to an ear of the user 10. In an embodiment, the ear of the user 10 may have a non-linear characteristic. That is, the non-linear characteristic may refer to when a sound signal having a plurality of frequencies is output to the ear of the user 10, an inter-modulation distorted sound for a plurality of frequencies may be included in the reflection signal of the output sound signal. For example, the inter-modulation distorted sound included in the reflection signal may be a third-order low-frequency inter-modulation distorted sound.

Referring to FIG. 6A, the electronic device 100 may output, to the ear of the user 10 through the speaker 150, each of the sound signal 610 obtained by combining a first signal with a frequency of f1, a second signal with a frequency of f2, and a sound signal 620 that has been obtained by combining the first signal, the second signal, and an anti-phase signal 621 with a frequency of 2f1−f2, which is a frequency related to the distortion production otoacoustic emission of f1 and f2.

As shown in FIG. 6B, the electronic device 100 may measure the strength (e.g., signal-to-noise ratio (SNR)) of the signal of the frequency (e.g., third-order low frequency inter-modulation distortion) related to the distortion production otoacoustic emission included in the reflection signal obtained from the ear of the user 10. A speaker 150 may be disposed on each of both ears of the user 10, and the sound signal 610 or the sound signal 620 may be output through each speaker 150.

In an embodiment, the strength of the signal 630 having the frequency related to the distortion production otoacoustic emission that is included in the reflection signal of the sound signal 610, which has been obtained by combining the first signal with a frequency of f1 and the second signal with a frequency of f2, may be approximately 6 dB for the left ear and approximately 5.5 dB for the right ear, for example.

However, the strength of the signal 640 having the frequency related to the distortion production otoacoustic emission that has been included in the reflection signal of the sound signal 620 may be approximately 19 dB for the left ear and approximately 19 dB for the right ear, for example.

Thus, it may be identified that if the anti-phase signal with a frequency of 2f1−f2, which is a frequency related to the distortion production otoacoustic emission of f1 and f2, is not combined, then the distortion production otoacoustic emission signal generated from the user's ear may be canceled out with the inter-modulation distorted signal with a frequency of f1 and f2 output through the speaker 150. Consequently, the measured distortion production otoacoustic emission signal may be low, which may result to an incorrect determination as to hearing loss, despite the user having normal hearing.

FIG. 6B illustrates that when the anti-phase signal is not applied, the distortion production otoacoustic emission signal generated from the user's ear may be canceled out with the inter-modulation distorted signals of f1 and f2 output through the speaker 150. Alternatively or additionally, the distortion production otoacoustic emission signal generated from the user's ear may be reinforced. As a result, it may be difficult to precisely measure the user's hearing.

However, if the anti-phase signal with a frequency of 2f1−f2, which is a frequency related to the distortion production otoacoustic emission of f1 and f2, is combined with the output sound signal, the inter-modulation distorted signals of f1 and f2 output through the speaker 150 may have already been canceled, so that the distortion production otoacoustic emission signal generated from the user's ear may be normally measured, allowing for an accurate hearing test.

Figure 7:
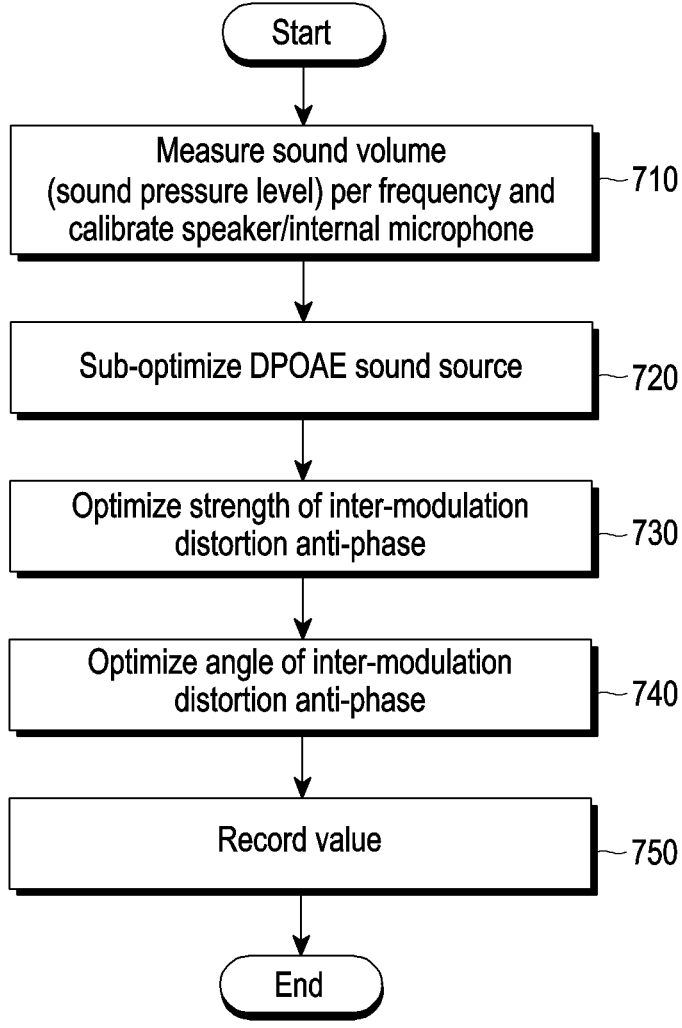
FIG. 7 is a view illustrating an operation for determining an anti-phase signal of a distortion production otoacoustic emission frequency to be combined with a sound signal, according to an embodiment of the disclosure.

FIG. 7 is a view illustrating an operation for determining an anti-phase signal of a distortion production otoacoustic emission frequency to be combined with a sound signal, according to an embodiment of the disclosure.

Referring to FIG. 7, in operation 710, the electronic device 100 of the disclosure may measure the sound volume (e.g., sound pressure level (dB SPL)) per frequency and calibrate the speaker 150 and the internal microphone 160. According to various embodiments, calibration may be performed before the electronic device 100 is shipped out from the manufacturer. In other optional or additional embodiments, the calibration may be performed by a user after the electronic device 100 has been shipped out from the manufacturer.

According to various embodiments, the electronic device 100 may output the sound signal through the speaker 150, while changing the sound volume per frequency of the sound signal. The electronic device 100 may compare the output sound signal with a result of a measurement using a sound level meter. The comparison result is described with reference to FIG. 8A.

According to an optional or additional embodiment, the electronic device 100 may compare the result of the measurement using the sound level meter for the sound signal output through the speaker 150 and the result of the measurement through the microphone 160 of the electronic device 100. The comparison result is described with reference to FIG. 8B.

Figure 8A:
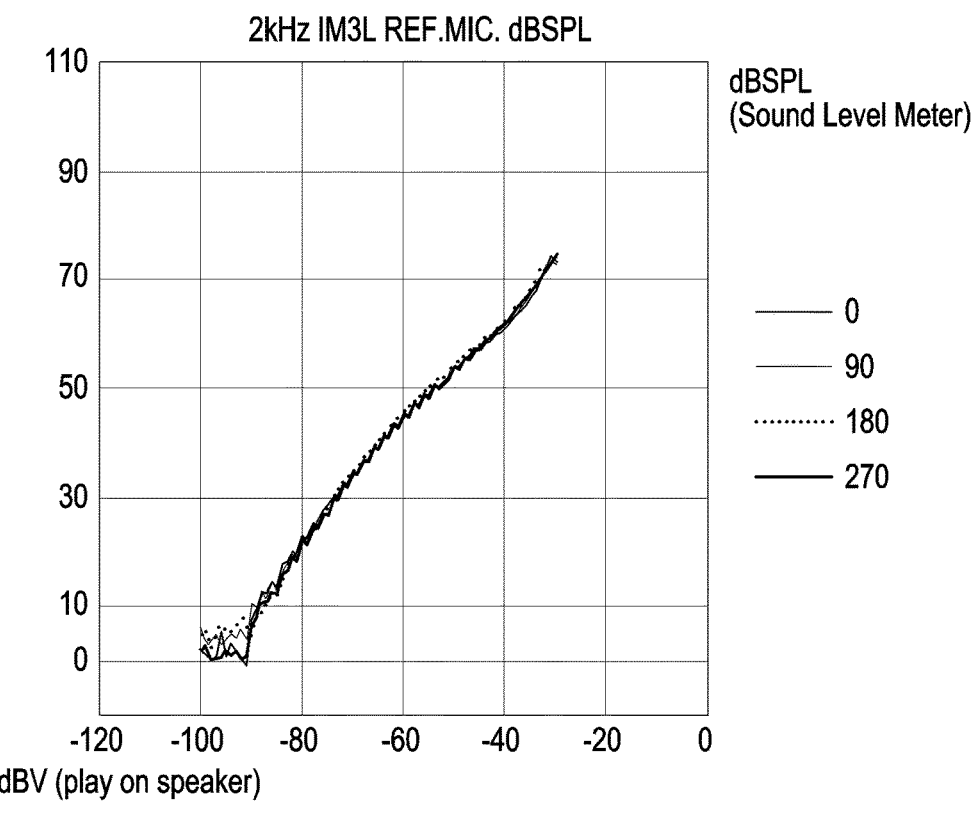
FIGS. 8A and 8B are views illustrating an operation for determining an anti-phase signal of a distortion production otoacoustic emission frequency to be combined with a sound signal, according to an embodiment of the disclosure.

FIG. 8A is a view illustrating the results of a comparison between the sound volume of the sound signal (e.g., pure tone signal) output from the speaker 150 of the electronic device 100 and the sound volume measured by the sound level meter.

For example, the electronic device 100 may sequentially change (e.g., from −30 dBV to −120 dBV) the sound volume of the sound signal (e.g., pure tone signal) having a specific frequency (e.g., f1 or 2 kHz) and a specific phase (e.g., 0°, 90°, 180°, 270°) while outputting through the speaker 150 and measure the sound volume of the output sound signal using the sound level meter.

For example, as shown in FIG. 8A, when the sound volume of the sound signal output from the speaker 150 is proportional to the sound volume of the sound signal measured by the sound level meter, it may be identified that the output of the speaker 150 is normal. If there is a particular range in which the sound volumes are not proportional, the electronic device 100 may calibrate the characteristics of the speaker 150 in the particular range.

Figure 8B:
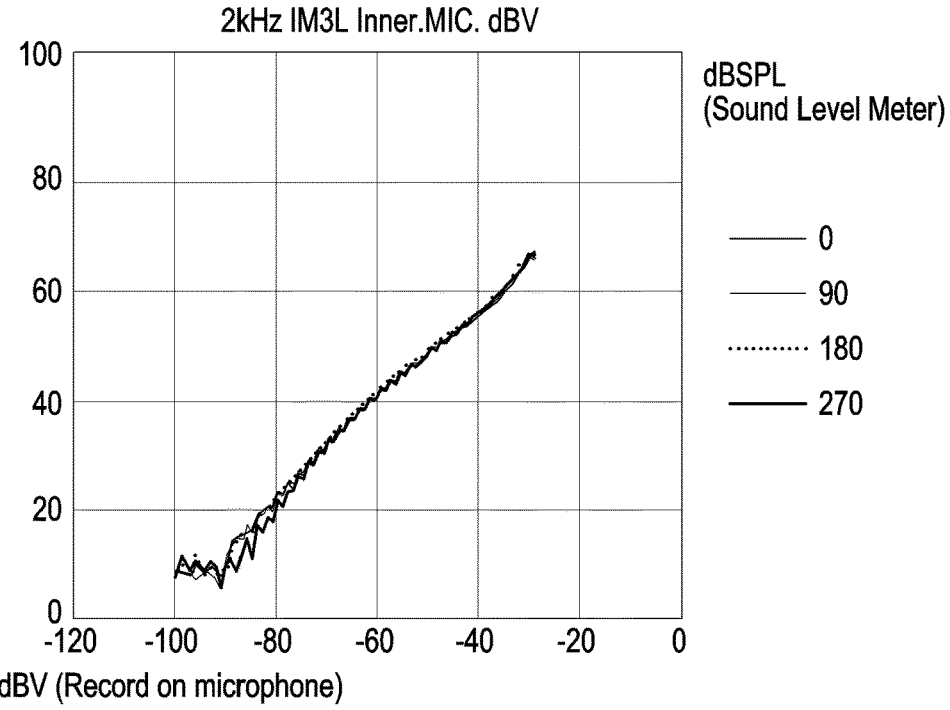

FIG. 8B is a view illustrating the results of a comparison between the sound volume of the sound signal input through the microphone 160 of the electronic device 100 and the sound volume of the sound signal measured by the sound level meter. The sound signal input through the microphone 160 and the sound signal measured by the sound level meter may be signals output through the speaker 150 of the electronic device 100.

For example, the electronic device 100 may sequentially change (e.g., from −30 dBV to −120 dBV) the sound volume of the sound signal (e.g., pure tone signal) having a specific frequency (e.g., f1 or 2 kHz) and a specific phase (e.g., 0°, 90°, 180°, 270°) while outputting through the speaker 150 and measure the sound volume of the output sound signal using the sound level meter.

For example, as shown in FIG. 8B, when the sound volume of the sound signal input to the microphone 160 is proportional to the sound volume of the sound signal measured by the sound level meter, it may be identified that the input of the microphone 160 is normal. If there is a particular range in which the sound volumes are not proportional is included, the electronic device 100 may calibrate the characteristics of the microphone 160 in the particular range.

Returning to FIG. 7, according to various embodiments, in operation 720, the electronic device 100 may sub-optimize the sound source of the DPOAE. For example, the electronic device 100 may identify whether the sound volume of the input signal is the expected sound volume for achieving the expected output sound volume of the sound signal to be used for a hearing test using distortion production otoacoustic emission. According to various embodiments, in operation 720, the signal with the frequency (e.g., 2f1−f2) related to distortion production otoacoustic emission may not be included in the output sound signal.

For example, the electronic device 100 may output the sound signal, in which the signals of the plurality of frequencies (e.g., f1 and f2) each having a specific sound volume are combined, to the 2 cc coupler 20 through the speaker 150, receive the signal reflected from the 2 cc coupler 20 through the microphone 160, and identify the input sound volume relative to the output sound volume.

According to various embodiments, in operation 730, the electronic device 100 may optimize the strength of the inter-modulation distortion anti-phase signal. For example, the frequency of the inter-modulation distortion anti-phase signal may be a frequency (e.g., 2f1−f2) related to the distortion production otoacoustic emission for the two frequencies (e.g., f1 and f2). Hereinafter, the frequency related to distortion production otoacoustic emission may be denoted as 2f1–f2 for convenience of description.

According to various embodiments, the electronic device 100 may output the signal to the 2 cc coupler 20 through the speaker 150 while changing (e.g., from –30 dBV to –120 dBV) the strength of the anti-phase signal with frequency of 2f1–f2 included in the sound signal and measure the strength of the anti-phase signal of 2f1–f2 included in the sound signal input through the microphone 160. The measurement result is described with reference to FIG. 9.

Figure 9:
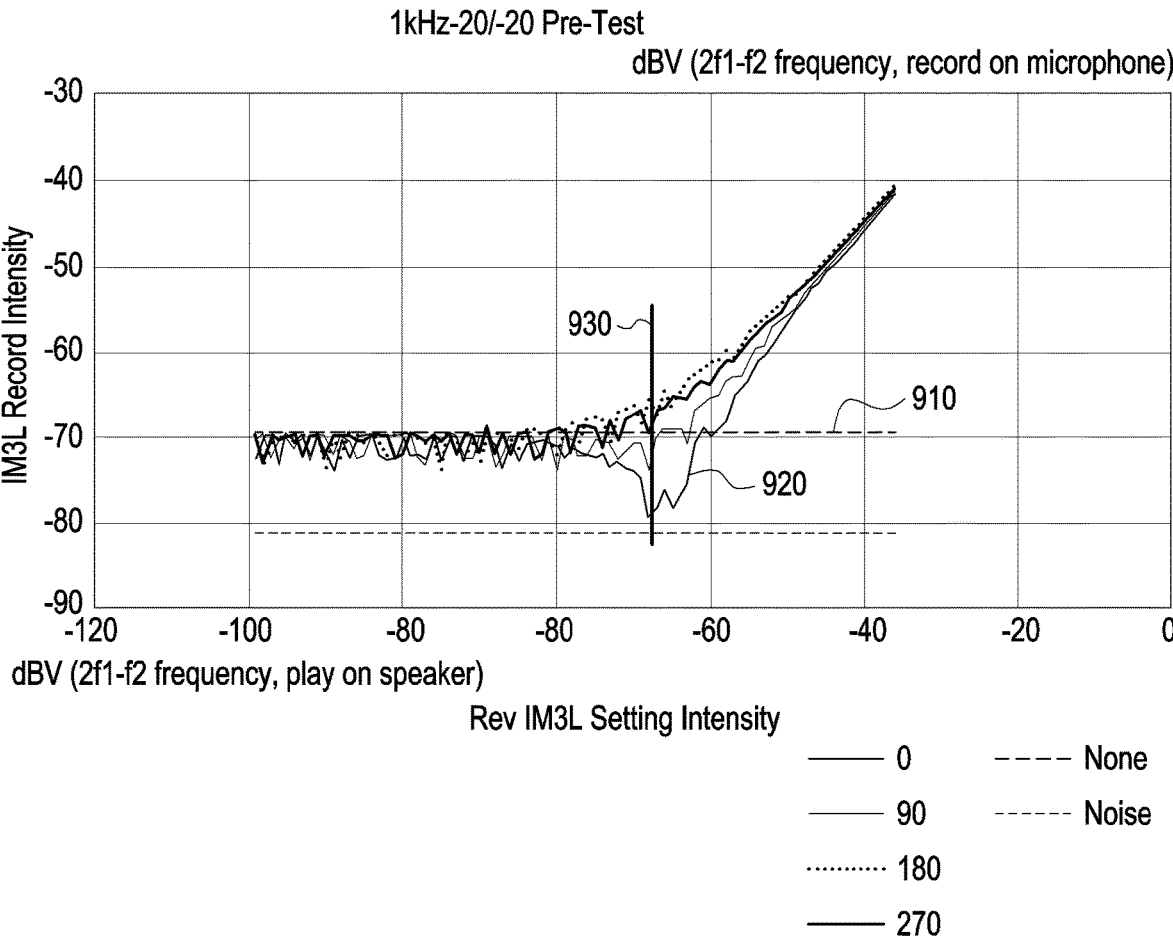
FIG. 9 is a view illustrating an operation for determining an anti-phase signal of a distortion production otoacoustic emission frequency to be combined with a sound signal, according to an embodiment of the disclosure.

FIG. 9 is a view illustrating the strength of an anti-phase signal of 2f1–f2 included in the sound signal output through the speaker 150 and the strength of the anti-phase signal of 2f1–f2 included in the sound signal input through the microphone 160. According to various embodiments, FIG. 9 includes the measurement results of each of the sound signal including the f1 signal and the f2 signal having a phase of 0° and the sound signal including the 2f1–f2 signals having different phases of 0°, 90°, 180°, and 270°, for example.

Referring to FIG. 9, when the sound signal in which only the signals of the two frequencies are combined is output through the speaker 150, it is identified that the magnitude of the inter-modulation distorted sound 910 of 2f1–f2 included in the sound signal input through the microphone 160 is approximately, –70 dBV, for example.

According to various embodiments, when the sound signal in which the anti-phase signal with frequency of 2f1–f2 is combined with the signals of two frequencies (e.g., f1 and f2), each having a specific sound volume, is output through the speaker 150, it may be identified that the strength of the signal with frequency of 2f1–f2 of the sound signal input through the microphone 160 at a specific strength of the anti-phase signal with frequency of 2f1–f2 included in the sound signal output through the speaker 150 is reduced.

For example, referring to FIG. 9, when the phase of the anti-phase signal with frequency of 2f1–f2 included in the sound signal output through the speaker 150 is 0°, and the strength is approximately –70 dBV, the strength of the signal with frequency of 2f1–f2 of the sound signal input through the microphone 160 may be minimized. For that reason, the inter-modulation distorted sound with frequency of 2f1–f2 generated when f1 and f2 are combined in the filter of the speaker 150 is canceled out by the anti-phase signal with frequency of 2f1–f2 with a phase of 0° and a strength of approximately –70 dBV combined with f1 and f2.

According to various embodiments, referring to FIG. 9, it may be identified that the optimal strength 930 of the anti-phase signal with frequency of 2f1–f2 in the electronic device 100 is approximately –70 dBV, for example.

In operation 730 described above, the strength of the signal with frequency of 2f1–f2 input through the microphone 160, when the anti-phase signal with frequency of 2f1–f2 is not combined, is measured, and the strength of the anti-phase signal with frequency of 2f1–f2 in which the strength of the signal with frequency of 2f1–f2 input through the microphone 160 is reduced is measured while changing the strength of the anti-phase signal of 2f1–f2. However, according to various embodiments, when combining f1 and f2 and outputting it, the electronic device 100 may estimate the strength of the signal with frequency of 2f1–f2 to be input through the microphone 160. The electronic device 100 may calculate the strength of the anti-phase signal with frequency of 2f1–f2 to be combined with the sound signal to be output through the speaker 150, based on the estimated strength of the signal with frequency of 2f1–f2.

Returning to FIG. 7, according to various embodiments, in operation 740, the electronic device 100 may optimize the angle (e.g., phase) of the inter-modulation distortion anti-phase signal.

For example, the electronic device 100 may output the sound signal obtained by combining the first signal f1 and the second signal f2 having a specific sound volume and the anti-phase signal with frequency of 2f1–f2 with a determined strength through the speaker 150 to the 2 cc coupler 20 and measure the strength of the signal with frequency of 2f1–f2 included in the sound signal input through the microphone 160. According to various embodiments, the electronic device 100 may fix the phases of the f1 signal and the f2 signal included in the sound signal output through the speaker 150 to 0°, for example, while changing the phase of the anti-phase signal with frequency of 2f1–f2 (e.g., 0° to 360°). For example, the electronic device 100 may change the phase of the anti-phase signal with frequency of 2f1–f2 in units of 1°. The result of measuring the strength of the signal with frequency of 2f1–f2 included in the sound signal input through the microphone 160 while changing the phase of the anti-phase signal with frequency of 2f1–f2 included in the sound signal output through the speaker 150 is described with reference to FIG. 10.

Figure 10:
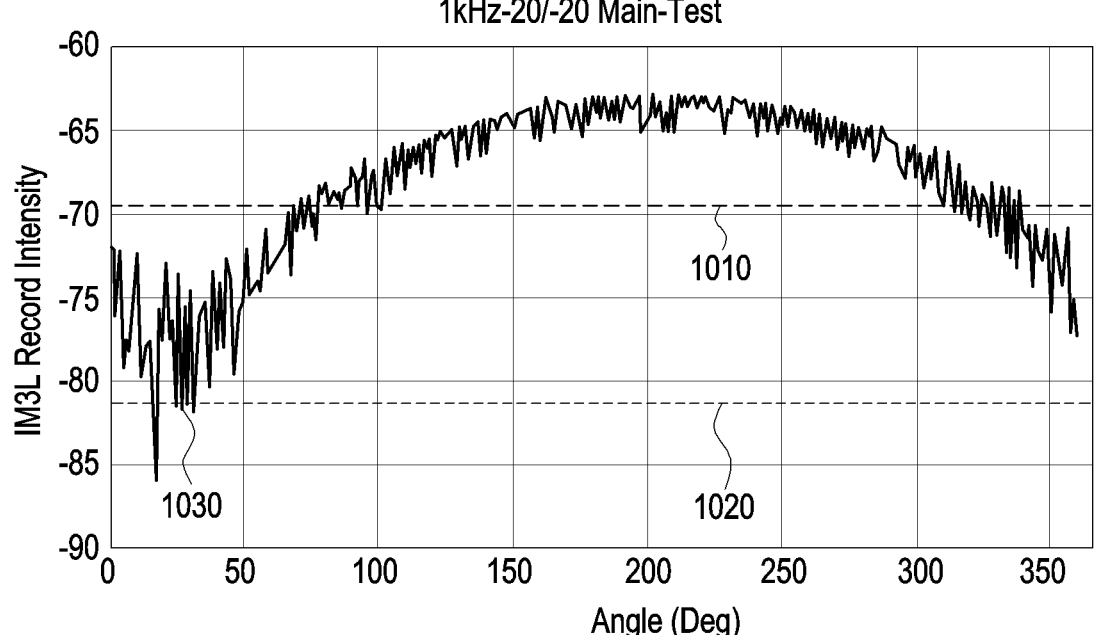
FIG. 10 is a view illustrating an operation for determining an anti-phase signal of a distortion production otoacoustic emission frequency to be combined with a sound signal, according to an embodiment of the disclosure.

Referring to FIG. 10, the strength of the signal 1010 of 2f1–f2 included in the sound signal input through the microphone 160 when outputting a sound signal not including the anti-phase signal of 2f1–f2 through the speaker 150 may be approximately –70 dBV, for example.

According to various embodiments, referring to FIG. 10, when the phase of the anti-phase signal with frequency of 2f1–f2 included in the sound signal to be output through the speaker 150 is 25°, the strength of the signal 1020 with frequency of 2f1–f2 input through the microphone 160 may be as low as approximately –81 dBV, for example. For this reason, the inter-modulation distorted sound with frequency of 2f1–f2 generated when f1 and f2 are combined in the filter of the speaker 150 is canceled out (or significantly reduced) by the anti-phase signal (or significantly reduced) of 2f1–f2 with a phase of 25° combined with f1 and f2.

According to various embodiments, referring to FIG. 10, it may be identified that the optimal angle 1030 of the anti-phase signal with frequency of 2f1–f2 in the electronic device 100 is approximately 25°, for example.

Returning to FIG. 7, according to various embodiments, in operation 750, the electronic device 100 may record the measured values.

For example, the electronic device 100 may store values for the calibration value of the speaker 150 for each frequency (e.g., f1 and f2), the calibration value of the microphone 160 for each frequency, the magnitude of the signal of the frequency related to distortion production otoacoustic emission generated due to the combination of the frequencies in the filter, the strength of the signal of each frequency, the strength of the anti-phase signal of the signal of the frequency related to distortion production otoacoustic emission, and the angle.

According to various embodiments, when the strength of the signal of the frequency related to distortion production otoacoustic emission generated due to the combination in the filter is less than a set value, the strength of the anti-phase signal of the signal of the frequency related to distortion production otoacoustic emission may be zero (0), for example. Accordingly, the strength of the anti-phase signal of the signal of the frequency related to distortion production otoacoustic emission included in the protocol may be zero (0), for example.

According to various embodiments, the measured values may be stored in the electronic device 100 or be transmitted to an external device 200 through the communication module of the electronic device 100 and stored in the external device 200.

In some embodiments, when a cradle device corresponding to the electronic device 100 is manufactured in the form of having a space with a volume (e.g., 2 cc) similar to the volume of the outer ear of the user, if contact between the cradle device and the electronic device 100 is detected, the electronic device 100 may perform calibration on the speaker 150 and the microphone 160 using the space of the cradle device. For example, the cradle device may be a device for charging and/or storing the electronic device 100.

According to various embodiments, the electronic device 100 may obtain a characteristic value in the 2 cc coupler 20 by adding a calibration value to a characteristic value in the cradle device using a conversion function between the characteristic of the sound signal per frequency in the cradle device and the characteristic of the sound signal per frequency in the 2 cc coupler 20. Thus, the cradle device may replace the 2 cc coupler 20.

Figure 11:
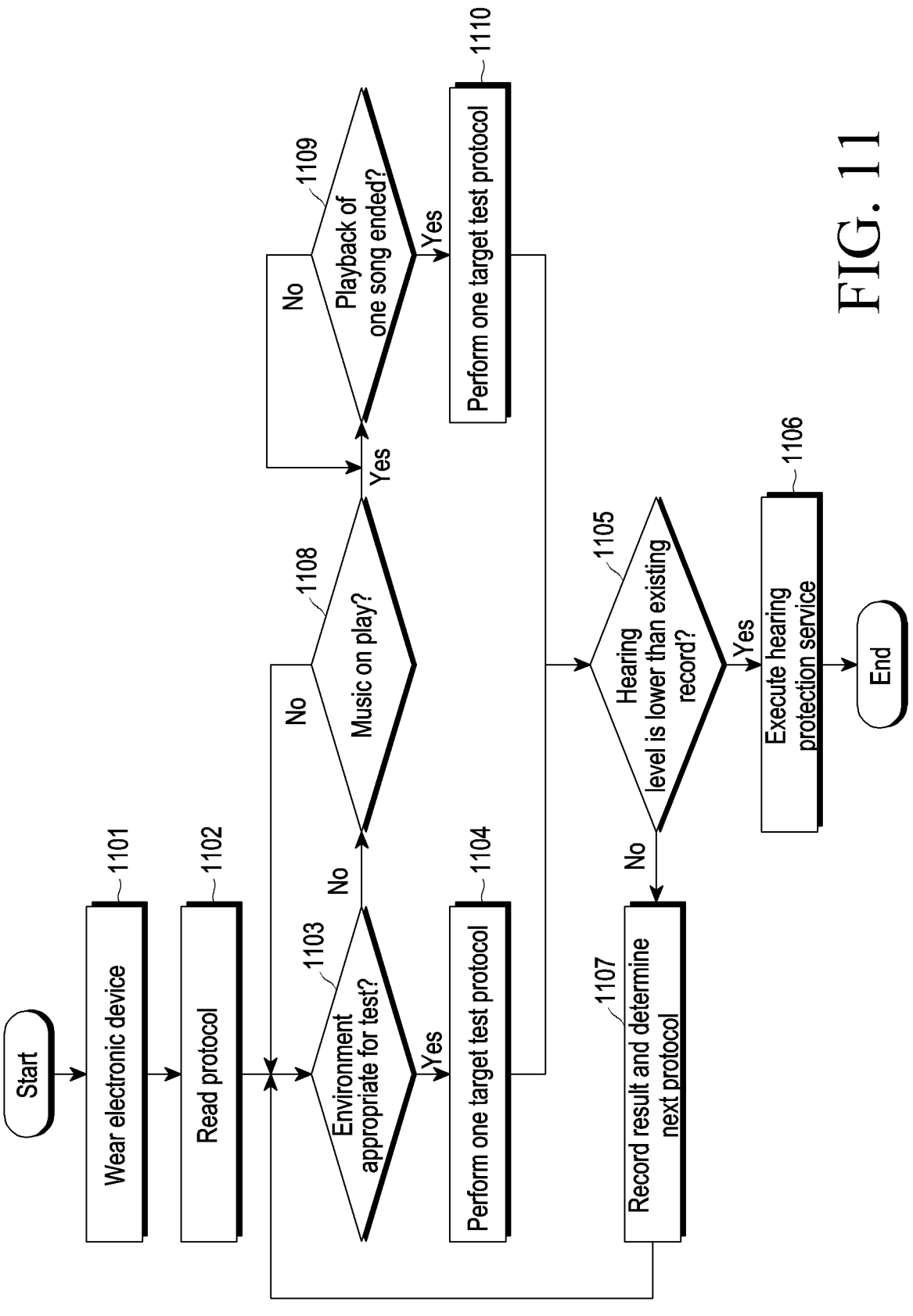
FIG. 11 is a view illustrating a hearing test operation by an electronic device, according to an embodiment of the disclosure.

FIG. 11 is a view illustrating a hearing test operation by an electronic device 100, according to an embodiment of the disclosure.

According to various embodiments, in operation 1101, the electronic device 100 may detect being worn on the user's ear. For example, the electronic device 100 may determine whether it is worn on the user's ear using an included sensor (e.g., proximity sensor, contact sensor, illuminance sensor, or the like).

According to various embodiments, in operation 1102, the electronic device 100 may obtain a protocol. For example, the electronic device 100 may obtain a plurality of protocols stored in the memory 110 and/or a plurality of protocols received from an external device 200. According to various embodiments, each protocol of the plurality of protocols may include information about the frequencies of two pure tone signals, information about the frequency related to distortion production otoacoustic emission of the two pure tone signals, information about the strengths of the two pure tone signals, information about the strength of the anti-phase signal of the frequency related to the distortion production otoacoustic emission, and information about the angle of the anti-phase signal of the frequency related to the distortion production otoacoustic emission.

According to various embodiments, in operation 1103, the electronic device 100 may determine whether the environment is appropriate for a hearing test. For example, if a set period (e.g., one month or one week) elapses after the previously performed hearing test, the electronic device 100 may determine that the environment is appropriate for a hearing test. Alternatively or additionally, if the set period has not elapsed since the last performed hearing test, the electronic device 100 may determine that the environment is not appropriate for a hearing test.

In an optional or additional embodiment, the electronic device 100 may identify whether the noise in the ambient environment is less than a set value. For example, if the strength of the sound signal (e.g., noise) received through the microphone 160 before outputting the sound signal for the hearing test is less than a set value, the electronic device 100 may determine that the environment is appropriate for the hearing test. Alternatively or additionally, if the strength of the sound signal (e.g., noise) received through the microphone 160 before outputting the sound signal for the hearing test exceeds the set value, the electronic device 100 may determine that the environment is not appropriate for the hearing test.

In another optional or additional embodiment, the electronic device 100 may determine that the environment is not appropriate for the hearing test if a content sound signal is being output through the speaker 150. For example, if music is playing, the sound signal of video content is being output, or a voice and/or video call is being output through the speaker 150, the electronic device 100 may determine that the environment is not appropriate for the hearing test. Alternatively or additionally, the electronic device 100 may determine that the environment is appropriate for the hearing test if no audio signal is being output through the speaker. That is, if no music is playing, no sound signal of video content is being output, and a voice call is not being output through the speaker 150, the electronic device 100 may determine that the environment is appropriate for the hearing test.

In some embodiments, in operation 1103, the electronic device 100 may combine one or more of the conditions described above in order to determine whether the environment is appropriate for the hearing test. For example, the electronic device 100 may determine that the environment is appropriate for the hearing test when the strength of the sound signal (e.g., noise) received through the microphone 160 before outputting the sound signal for the hearing test is less than the set value and the set period has elapsed since the last performed hearing test. However, the present disclosure is not limited in this regard. For example, the electronic device 100 may determine whether the environment is appropriate for the hearing test based on other combination of conditions without departing from the scope of the present disclosure.

According to various embodiments, upon determining that the environment is appropriate for the hearing test (YES in operation 1103), the electronic device 100 may perform one target test protocol from among the plurality of protocols in operation 1104.

For example, the electronic device 100 may output, through the speaker 150, the sound signal obtained by combining the two frequency signals related to the hearing frequency range to be tested and the signal of the frequency related to the distortion production otoacoustic emission of the two frequencies based on one protocol and measure the strength of the signal of the frequency related to the distortion production otoacoustic emission included in the sound signal input through the microphone 160, thereby testing the user's hearing.

According to various embodiments, in operation 1105, the electronic device 100 may determine whether the hearing level is lower than the existing record. For example, when the user's previous hearing test result is stored, the electronic device 100 may compare the previous hearing test result with the current hearing test result, determining whether the user's hearing level is reduced. In an optional or additional embodiment, the electronic device 100 may compare a set normal value with the current hearing test result, determining whether the user's hearing level is within the normal range of values.

According to various embodiments, upon determining that the user's hearing level is lower than the existing record (YES in operation 1105), the electronic device 100 may execute a hearing protection service in operation 1106. For example, the electronic device 100 may provide feedback for hearing protection. In an embodiment, when the electronic device 100 includes a display, the electronic device 100 may display a message through the display and/or transmit a message to an external device 200 to display the message on the display of the external device 200. Alternatively or additionally, the electronic device 100 may output an audible notification through the speaker 150. The audible notification may include, but not be limited to, a tone, a beep, a pre-recorded audio snippet/file, a voice, and the like.

According to various embodiments, the electronic device 100 may provide feedback recommending ear rest, in-depth test, sound volume reduction, feedback indicating ear fatigue, and/or may automatically reduce the sound volume of the tested frequency range and output it.

According to various embodiments, upon determining that the user's hearing level maintains the existing record or is better (NO in operation 1105), the electronic device 100 may record the test result of the tested frequency range and determine a next protocol to perform test in operation 1107. For example, the order of performing protocols may be set and the electronic device 100 may determine the next protocol to perform based on the set order. Alternatively or additionally, a protocol related to the frequency range in which a section with a large sound volume is frequently-used among the plurality of frequency ranges of the sound signal often listened to by the user, and the electronic device 100 may determine the next protocol to perform based on the use frequency of the protocols. However, the present disclosure is not limited in this regard. That is, the electronic device 100 may use other criteria, conditions, or techniques for selecting a next protocol to perform without deviating from the scope of the present disclosure.

According to various embodiments, before performing the next protocol, the electronic device 100 may return to operation 1103 to determine whether the environment is appropriate for the hearing test.

According to various embodiments, upon determining that the environment is inappropriate for the hearing test (NO in operation 1103), the electronic device 100 may determine whether music is playing in operation 1108. According to various embodiments, if music is not playing (NO in operation 1108), the electronic device 100 may return to operation 1103 to determine whether it is an environment appropriate for the hearing test. According to various embodiments, the electronic device 100 may provide feedback to the user to request to move a quiet environment and/or request to rewear (e.g., reposition) the electronic device 100.

In an optional or additional embodiment, if music is playing (YES in operation 1108), the electronic device 100 may determine whether playback of one song is ended in operation 1109. If playback of one song is not ended (NO in operation 1109), the electronic device 100 may determine again whether playback of one song is ended. When playback of one song is ended (YES in operation 1109), the electronic device 100 may perform one target test protocol in operation 1110. For example, the electronic device 100 may perform one test protocol before playing the next song after playback of one song is ended.

For example, the electronic device 100 may output, through the speaker 150, the sound signal obtained by combining the two frequency signals related to the hearing frequency range to be tested and the signal of the frequency related to the distortion production otoacoustic emission of the two frequencies based on one protocol and measure the strength of the signal of the frequency related to the distortion production otoacoustic emission included in the sound signal input through the microphone 160, thereby testing the user's hearing.

FIG. 11 illustrates that a hearing test is performed between song playbacks but, according to various embodiments, the electronic device 100 may play music for a hearing test reflecting a hearing test protocol or play a sound signal (e.g., music) of sound signal-inserted content based on the hearing test protocol. For example, the electronic device 100 may analyze the sound signal of the content and insert a hearing test protocol-based sound signal to a section where insertion of the hearing test protocol-based sound signal does not bother listening to the content sound signal.

According to various embodiments, the electronic device 100 may perform at least one of operation 1105, operation 1106, or operation 1107 based on the result of performing the protocol in operation 1110, as described above.

Figure 12:
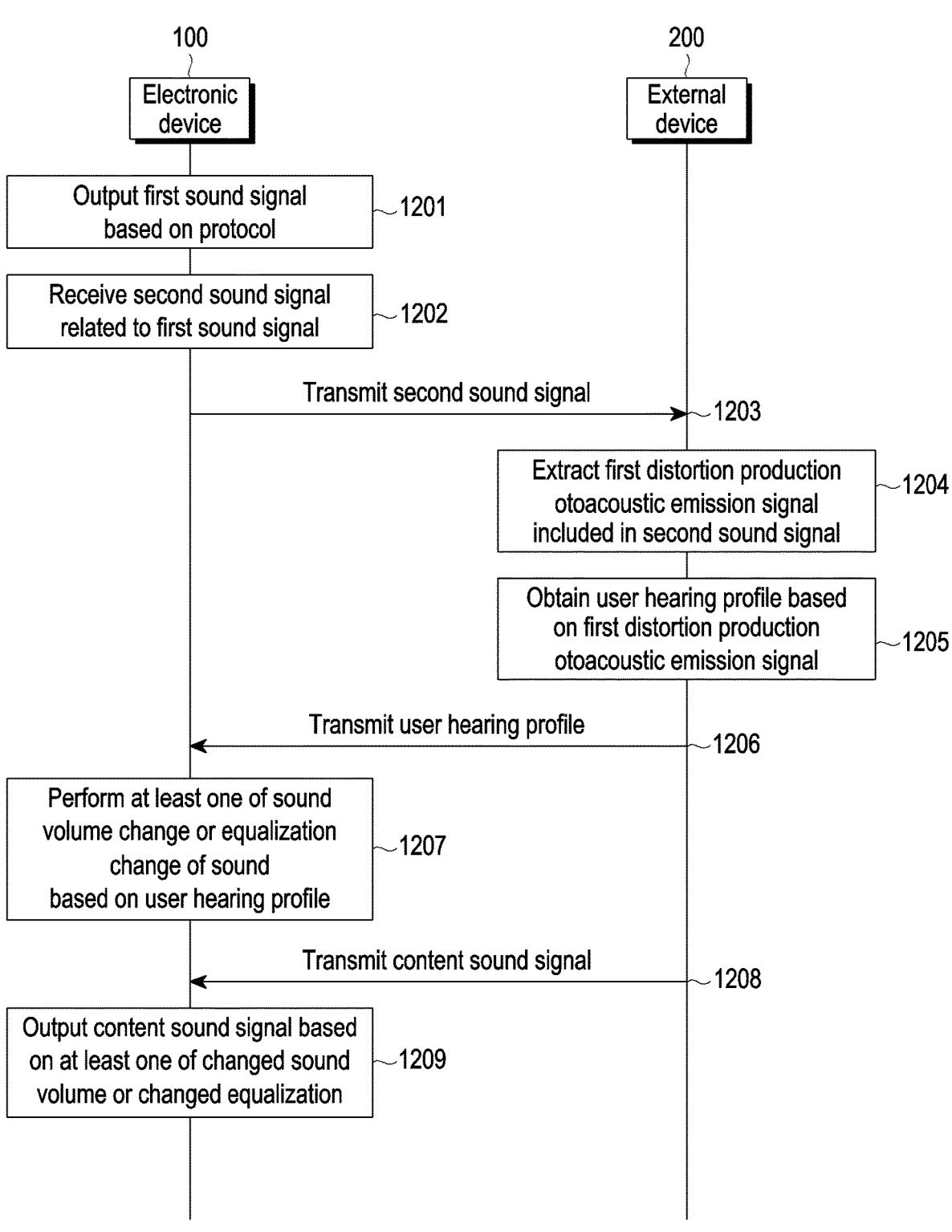
FIG. 12 is a view illustrating an operation for outputting a sound signal based on a user's hearing profile obtained according to an embodiment of the disclosure.

FIG. 12 is a view illustrating an operation for outputting a sound signal based on a user's hearing profile obtained according to an embodiment of the disclosure. The following description assumes that the wearing of the electronic device 100 on the user's ear is detected. A hearing test may be performed based on a set period (e.g., one month or one week), whenever the electronic device 100 is worn on the user's ear, or when the user inputs a manipulation command for a hearing test.

According to various embodiments, referring to FIG. 12, in operation 1201, the electronic device 100 may output a first sound signal based on a protocol. For example, the electronic device 100 may output, through the speaker 150, a first sound signal obtained by combining two frequency signals related to a hearing frequency range to be tested based on the protocol and a signal of a frequency related to distortion production otoacoustic emission of the two frequencies.

According to various embodiments, the protocol may be stored in the electronic device 100 and/or may be received from an external device 200. For example, the external device 200 is a device configured to communicate with the electronic device 100. In an embodiment, the external device 200 may include a terminal device connected with the electronic device 100, which may include an earphone, for example.

According to various embodiments, in operation 1202, the electronic device 100 may receive a second sound signal related to the first sound signal through the microphone 160.

According to various embodiments, in operation 1203, the electronic device 100 may transmit the received second sound signal to the external device 200.

According to various embodiments, in operation 1204, the external device 200 may extract a first distortion production otoacoustic emission signal included in the second sound signal received from the electronic device 100.

FIG. 12 illustrates that the external device 200 extracts the first distortion production otoacoustic emission signal included in the second sound signal received from the electronic device 100. However, according to various embodiments, the electronic device 100 may extract the first distortion production otoacoustic emission signal included in the second sound signal and transmit the extracted first distortion production otoacoustic emission signal to the external device 200.

According to various embodiments, in operation 1205, the external device 200 may obtain the user's hearing profile based on the first distortion production otoacoustic emission signal. FIG. 12 illustrates that the user's hearing profile is obtained based on the first distortion production otoacoustic emission signal obtained based on one protocol. However, according to various embodiments, the external device 200 may obtain the user's hearing profile for a plurality of frequency ranges based on a plurality of distortion production otoacoustic emission signals obtained based on a plurality of protocols. According to various embodiments, the external device 200 may store the obtained user hearing profile.

According to various embodiments, in operation 1206, the external device 200 may transmit the user hearing profile to the electronic device 100.

According to various embodiments, in operation 1207, the electronic device 100 may perform at least one of sound volume change or equalization change based on the user hearing profile received from the external device 200.

For example, upon determining that the user's hearing is deteriorated based on the user hearing profile, the electronic device 100 may reduce the sound volume. In an optional or additional embodiment, the electronic device 100 may change the equalization to reduce the sound volume of a specific frequency signal in the sound signal based on the user hearing profile or change the equalization so that the difference between the strengths (e.g., sound volumes) of the plurality of frequencies included in the sound signal to be output falls within a set range. Thus, it may be possible to obtain equalization customized for each user to fit the user's hearing condition.

According to various embodiments, the electronic device 100 may provide visual feedback (e.g., display of a message) and/or audible feedback (e.g., output of a notification) indicating that the user's hearing is deteriorated. According to various embodiments, the external device 200 may also provide visual feedback and/or audible feedback to indicate that the user's hearing is deteriorated based on the obtained user hearing profile. Alternatively or additionally, the electronic device 100 may provide visual feedback and/or audible feedback to indicate that the user's hearing is outside and/or inside a normal range of values based on a comparison between a set of normal value ranges and the hearing test results.

According to various embodiments, in operation 1208, the external device 200 may transmit the content sound signal to the electronic device 100 and, in operation 1209, the electronic device 100 may output the content sound signal based on at least one of the changed sound volume or changed equalization.

Figure 13:
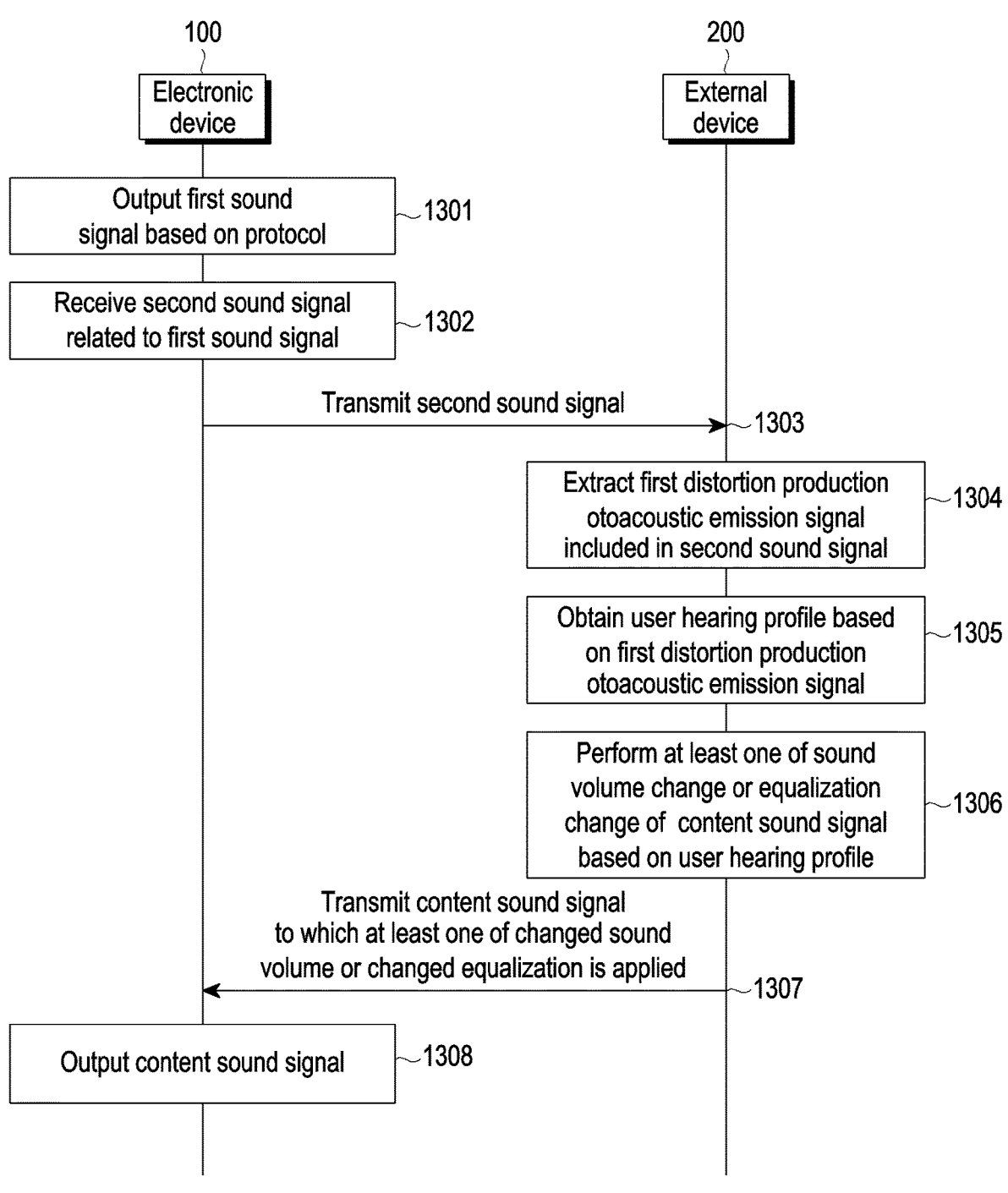
FIG. 13 is a view illustrating an operation for outputting a sound signal based on a user's hearing profile obtained according to an embodiment of the disclosure.

FIG. 13 is a view illustrating an operation for outputting a sound signal based on a user's hearing profile obtained according to an embodiment of the disclosure. The following description assumes that the wearing of the electronic device 100 on the user's ear is detected. A hearing test may be performed based on a set period (e.g., one month or one week), whenever the electronic device 100 is worn on the user's ear, or when the user inputs a manipulation command for a hearing test.

According to various embodiments, referring to FIG. 13, in operation 1301, the electronic device 100 may output a first sound signal based on a protocol. According to various embodiments, in operation 1302, the electronic device 100 may receive a second sound signal related to the first sound signal through the microphone 160.

According to various embodiments, in operation 1303, the electronic device 100 may transmit the received second sound signal to the external device 200. According to various embodiments, in operation 1304, the external device 200 may extract a first distortion production otoacoustic emission signal included in the second sound signal received from the electronic device 100.

FIG. 13 illustrates that the external device 200 extracts the first distortion production otoacoustic emission signal included in the second sound signal received from the electronic device 100. However, according to various embodiments, the electronic device 100 may extract the first distortion production otoacoustic emission signal included in the second sound signal and transmit the extracted first distortion production otoacoustic emission signal to the external device 200.

According to various embodiments, in operation 1305, the external device 200 may obtain the user's hearing profile based on the first distortion production otoacoustic emission signal. FIG. 13 illustrates that the user's hearing profile is obtained based on the first distortion production otoacoustic emission signal obtained based on one protocol. However, according to various embodiments, the external device 200 may obtain the user's hearing profile for a plurality of frequency ranges based on a plurality of distortion production otoacoustic emission signals obtained based on a plurality of protocols. According to various embodiments, the external device 200 may store the obtained user hearing profile.

Operations 1301 to 1305 in FIG. 13 are similar to operations 1201 to 1205 in FIG. 12, and thus, no duplicate description thereof is given for the sake of simplicity and brevity.

According to various embodiments, in operation 1306, the external device 200 may perform at least one of sound volume change or equalization change of the content sound signal based on the user's hearing profile.

For example, upon determining that the user's hearing is deteriorated based on the user hearing profile, the external device 200 may reduce the sound volume. In an embodiment, the external device 200 may change the equalization to reduce the sound volume of a specific frequency signal in the sound signal based on the user hearing profile or change the equalization so that the difference between the strengths (e.g., sound volumes) of the plurality of frequencies included in the sound signal to be output falls within a set range. Thus, it may be possible to obtain equalization customized for each user to fit the user's hearing condition.

According to various embodiments, in operation 1307, the external device 200 may transmit a content sound signal to which at least one of the changed sound volume or the changed equalization has been applied to the electronic device 100.

According to various embodiments, in operation 1308, the electronic device 100 may output the content sound signal received from the external device 200 through the speaker 150.

According to various embodiments, the electronic device 100 may provide visual feedback (e.g., display of a message) and/or audible feedback (e.g., output of a notification) indicating that the user's hearing is deteriorated. According to various embodiments, the external device 200 may also provide visual feedback and/or audible feedback to indicate that the user's hearing is deteriorated based on the obtained user hearing profile. Alternatively or additionally, the electronic device 100 may provide visual feedback and/or audible feedback to indicate that the user's hearing is outside and/or inside a normal range of values based on a comparison between a set of normal value ranges and the hearing test results.

Figure 14:
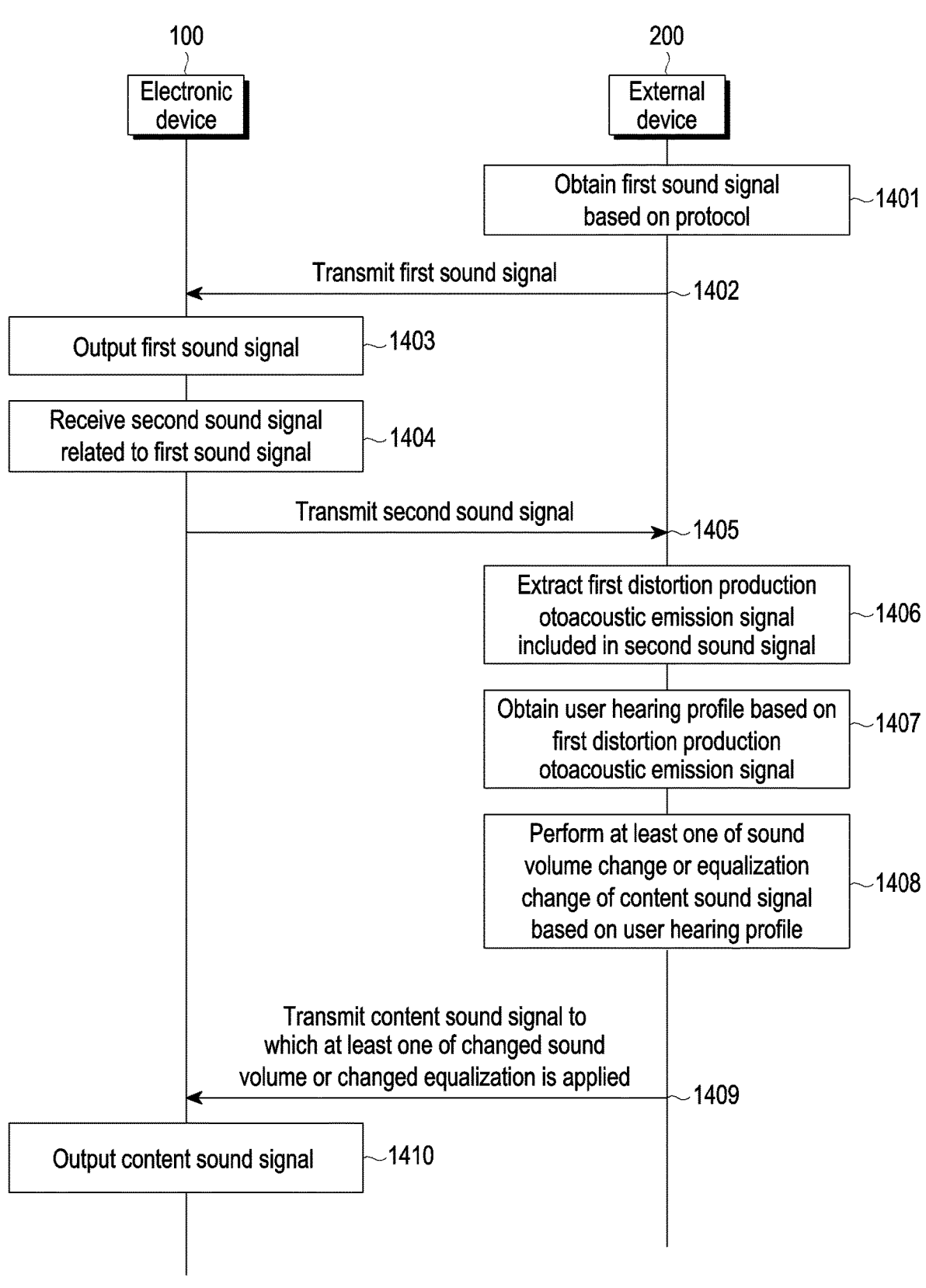
FIG. 14 is a view illustrating an operation for outputting a sound signal based on a user's hearing profile obtained according to an embodiment of the disclosure.

FIG. 14 is a view illustrating an operation for outputting a sound signal based on a user's hearing profile obtained according to an embodiment of the disclosure. For example, the external device 200 of FIG. 14 may perform generation and analysis of the sound signal for a hearing test of the disclosure, and the electronic device 100 may only perform the operations of outputting the sound signal received from the external device 200 and transmitting the sound signal input through the microphone 160 to the external device 200. The following description assumes that the wearing of the electronic device 100 on the user's ear is detected. A hearing test may be performed based on a set period (e.g., one month or one week), whenever the electronic device 100 is worn on the user's ear, or when the user inputs a manipulation command for a hearing test.

According to various embodiments, referring to FIG. 14, in operation 1401, the external device 200 may obtain a first sound signal based on a protocol. For example, the external device 200 may generate a first sound signal obtained by combining two frequency signals related to a hearing frequency range to be tested based on the protocol and a signal of a frequency related to distortion production otoacoustic emission of the two frequencies.

According to various embodiments, in operation 1402, the external device 200 may transmit the first sound signal to the electronic device 100 and, in operation 1403, the electronic device 100 may output the received first sound signal through the speaker 150.

According to various embodiments, in operation 1404, the electronic device 100 may receive a second sound signal related to the first sound signal through the microphone 160.

According to various embodiments, in operation 1405, the electronic device 100 may transmit the received second sound signal to the external device 200.

According to various embodiments, in operation 1406, the external device 200 may extract a first distortion production otoacoustic emission signal included in the second sound signal received from the electronic device 100.

According to various embodiments, in operation 1407, the external device 200 may obtain the user's hearing profile based on the first distortion production otoacoustic emission signal. FIG. 14 illustrates that the user's hearing profile is obtained based on the first distortion production otoacoustic emission signal obtained based on one protocol. However, according to various embodiments, the external device 200 may obtain the user's hearing profile for a plurality of frequency ranges based on a plurality of distortion production otoacoustic emission signals obtained based on a plurality of protocols. According to various embodiments, the external device 200 may store the obtained user hearing profile.

According to various embodiments, in operation 1408, the external device 200 may perform at least one of sound volume change or equalization change of the content sound signal based on the user's hearing profile.

According to various embodiments, in operation 1409, the external device 200 may transmit a content sound signal to which at least one of the changed sound volume or the changed equalization has been applied to the electronic device 100.

According to various embodiments, in operation 1410, the electronic device 100 may output the content sound signal received from the external device 200 through the speaker 150.

Operations 1404 to 1410 in FIG. 14 are similar to operations 1302 to 1308 in FIG. 13, and thus, no duplicate description thereof is given for the sake of simplicity and brevity.

Figure 15:
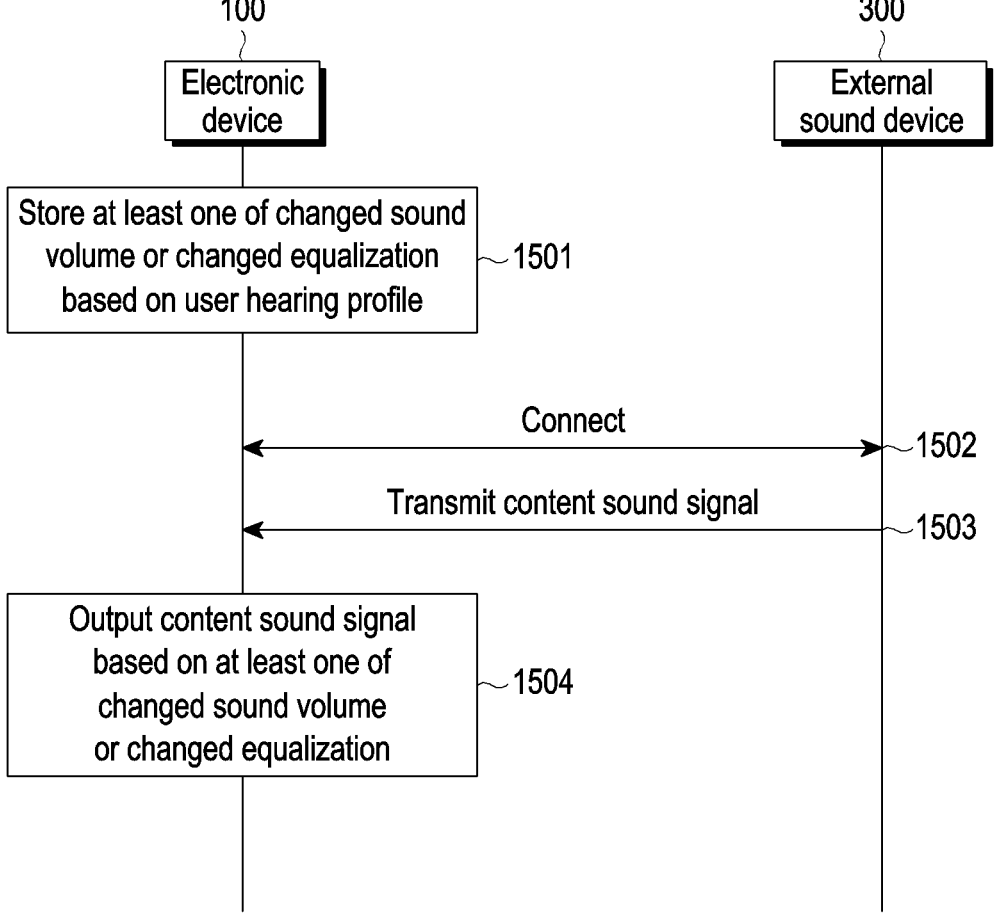
FIG. 15 is a view illustrating an operation for outputting a sound signal based on a user's hearing profile obtained according to an embodiment of the disclosure.

FIG. 15 is a view illustrating an operation for outputting a sound signal based on a user's hearing profile obtained according to an embodiment of the disclosure.

According to various embodiments, referring to FIG. 15, in operation 1501, the electronic device 100 may store at least one of the changed sound volume or the changed equalization based on the user hearing profile. According to various embodiments, the user hearing profile may be obtained by the electronic device 100 or obtained by a terminal device (e.g., the external device 200) connected with the electronic device 100 and received by the electronic device 100. According to various embodiments, the changed sound volume and/or the changed equalization may be one changed by the electronic device 100 or one changed by a terminal device connected with the electronic device 100 and received by the electronic device 100.

According to various embodiments, in operation 1502, the electronic device 100 may be connected with an external sound device 300. According to various embodiments, the external sound device 300 may be a terminal device (e.g., the external device 200) previously connected with the electronic device 100 or another external device 200 that may not be used in obtaining the user hearing profile. For example, the electronic device 100, which may include an earphone (or headset), may be connected to a different smartphone (e.g., external device 200) from a smartphone previously connected (e.g., external sound device 300), and/or a sound device.

According to various embodiments, in operation 1503, the external sound device 300 may transmit a content sound signal to the electronic device 100.

According to various embodiments, in operation 1504, the electronic device 100 may output the content sound signal based on at least one of the changed sound volume or the changed equalization. For example, the electronic device 100 may change at least one of the sound volume or equalization of the content sound signal received from the external sound device 300 based on the value stored in operation 1501 and output the changed content sound signal.

Figure 16:
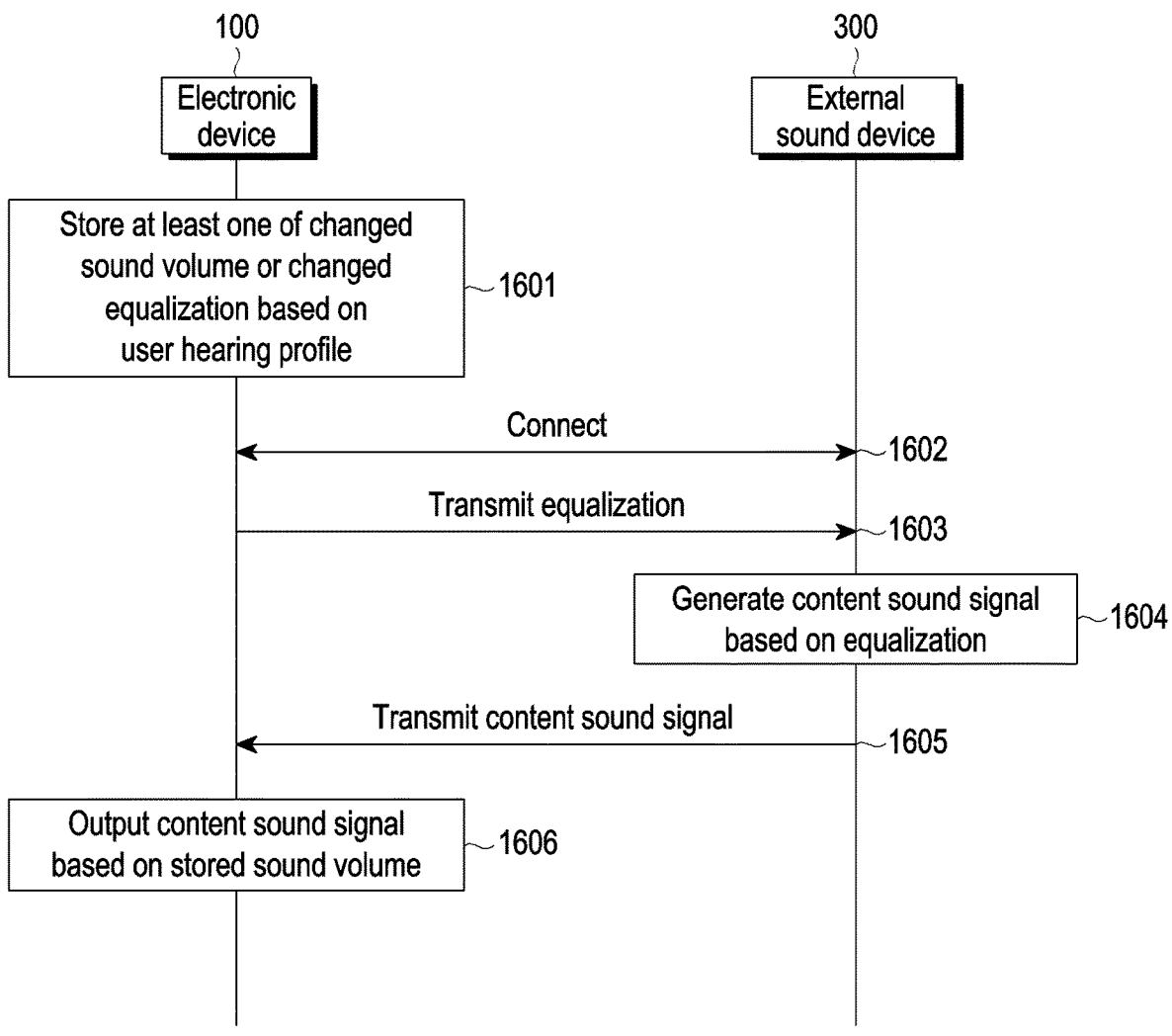
FIG. 16 is a view illustrating an operation for outputting a sound signal based on a user's hearing profile obtained according to an embodiment of the disclosure.

FIG. 16 is a view illustrating an operation for outputting a sound signal based on a user's hearing profile obtained according to an embodiment of the disclosure.

According to various embodiments, referring to FIG. 16, in operation 1601, the electronic device 100 may store at least one of the changed sound volume or the changed equalization based on the user hearing profile. According to various embodiments, the user hearing profile may be obtained by the electronic device 100 or obtained by a terminal device (e.g., the external device 200) connected with the electronic device 100 and received by the electronic device 100. According to various embodiments, the changed sound volume and/or the changed equalization may be one changed by the electronic device 100 or one changed by a terminal device connected with the electronic device 100 and received by the electronic device 100.

According to various embodiments, in operation 1602, the electronic device 100 may be connected with an external sound device 300. According to various embodiments, the external sound device 300 may be a terminal device (e.g., the external device 200) previously connected with the electronic device 100 or another external device 200 that may not be used in obtaining the user hearing profile. For example, the electronic device 100, which may include an earphone (or headset), may be connected to a different smartphone (e.g., external device 200) from a smartphone previously connected (e.g., external sound device 300), and/or a sound device.

According to various embodiments, in operation 1603, the electronic device 100 may transmit the stored equalization to the external sound device 300.

According to various embodiments, in operation 1604, the external sound device 300 may generate a content sound signal based on the received equalization.

FIG. 16 illustrates that the electronic device 100 transmits the equalization to the external sound device 300. However, according to various embodiments, the electronic device 100 may transmit a user hearing profile to the external sound device 300, and the external sound device 300 may generate a content sound signal in which the equalization has been changed, based on the received user hearing profile.

According to various embodiments, in operation 1605, the external sound device 300 may transmit a content sound signal to the electronic device 100. According to various embodiments, in operation 1606, the electronic device 100 may output the content sound signal based on the stored sound volume.

According to various embodiments of the disclosure, it may be possible to perform a hearing test based on distortion production otoacoustic emissions, only with one speaker 150 for each ear. Further, according to various embodiments of the disclosure, it is possible to reduce the user's hearing loss by obtaining an equalization customized to fit the user's hearing condition based on the user hearing profile.

According to various embodiments of the disclosure, an electronic device 100 may comprise a speaker 150, a microphone 160, a memory 110, a DSP 130, a driver 140 configured to convert a digital signal output from the DSP 130 into an analog signal and output the analog signal to the speaker 150, and a processor operatively connected with the speaker 150, the microphone 160, the memory 110, the DSP 130, and the driver 140. The processor may be configured to control the DSP 130 and the driver 140 to output, through the speaker 150, a first sound signal obtained by combining a signal of a first frequency, a signal of a second frequency, and an anti-phase signal of a third frequency related to a DPOAE of the first frequency and the second frequency, based on a first protocol among a plurality of protocols stored in the memory 110, upon receiving a second sound signal related to the first sound signal through the microphone 160, extract a first distortion production otoacoustic emission signal of the third frequency included in the second sound signal, control the DSP 130 and the driver 140 to output, through the speaker 150, a third sound signal obtained by combining a signal of a fourth frequency, a signal of a fifth frequency, and an anti-phase signal of a sixth frequency related to a DPOAE of the fourth frequency and the fifth frequency, based on a second protocol among the plurality of protocols, upon receiving a fourth sound signal related to the third sound signal through the microphone 160, extract a second distortion production otoacoustic emission signal of the sixth frequency included in the fourth sound signal, obtain a user hearing profile based on the first distortion production otoacoustic emission signal and the second distortion production otoacoustic emission signal, and perform at least one of a sound volume change or an equalization (EQ) change of a sound based on the user hearing profile.

According to various embodiments, the processor may be configured to change the equalization so that a difference in strength between a plurality of frequencies included in a sound to be output falls within a set range, based on the user hearing profile.

According to various embodiments, the processor may be configured to provide feedback to indicate that the user's hearing is deteriorated, based on the user hearing profile.

According to various embodiments, the processor may be configured to, if a strength of a sound signal received through the microphone 160 before outputting the first sound signal is less than a set value, output the first sound signal.

According to various embodiments, the processor may be configured to, if a content sound signal is being output through the speaker 150 before outputting the first sound signal, output the first sound signal after completing the output of the content sound signal.

According to various embodiments, the processor may be configured to output the first sound signal based on a set period.

According to various embodiments, each of the plurality of protocols may include information about frequencies of two pure tone signals, information about a frequency related to a distortion production otoacoustic emission of the two pure tone signals, information about strengths of the two pure tone signals, information about a strength of an anti-phase signal of a frequency related to the distortion production otoacoustic emission, and information about an angle of the anti-phase signal of the frequency related to the distortion production otoacoustic emission.

According to various embodiments, in at least some of the plurality of protocols, the strength of the anti-phase signal of the frequency related to the distortion production otoacoustic emission may be zero (0).

According to various embodiments, the electronic device 100 may further comprise an ear probe to be inserted into a user's outer ear. The speaker 150 and the microphone 160 may be disposed on a portion of the ear probe.

According to various embodiments, the processor may be configured to perform calibration on the speaker 150 and the microphone 160 upon detecting a contact of the electronic device 100 to a cradle device corresponding to the electronic device 100.

According to various embodiments, the electronic device 100 may further comprise a communication module. The processor may be configured to store at least one of the changed sound volume or the changed equalization, transmit the stored equalization to an external device 200 through the communication module, receive a content sound signal to which the stored equalization is applied, from the external device 200, and output the received content sound signal through the speaker based on the stored sound volume.

According to various embodiments, a method for controlling an electronic device 100 may comprise outputting, through a speaker 150 of the electronic device 100, a first sound signal obtained by combining a signal of a first frequency, a signal of a second frequency, and an anti-phase signal of a third frequency related to a DPOAE of the first frequency and the second frequency, based on a first protocol among a plurality of protocols stored in a memory 110 of the electronic device 100, upon receiving a second sound signal related to the first sound signal through a microphone 160 of the electronic device 100, extracting a first distortion production otoacoustic emission signal of the third frequency included in the second sound signal, outputting, through the speaker 150, a third sound signal obtained by combining a signal of a fourth frequency, a signal of a fifth frequency, and an anti-phase signal of a sixth frequency related to a DPOAE of the fourth frequency and the fifth frequency, based on a second protocol among the plurality of protocols, upon receiving a fourth sound signal related to the third sound signal through the microphone 160, extracting a second distortion production otoacoustic emission signal of the sixth frequency included in the fourth sound signal, obtaining a user hearing profile based on the first distortion production otoacoustic emission signal and the second distortion production otoacoustic emission signal, and performing at least one of a sound volume change or an equalization (EQ) change of a sound based on the user hearing profile.

According to various embodiments, performing at least one of the sound volume change or the equalization (EQ) change may change the equalization so that a difference in strength between a plurality of frequencies included in a sound to be output falls within a set range, based on the user hearing profile.

According to various embodiments, the method may further comprise providing feedback to indicate that the user's hearing is deteriorated, based on the user hearing profile.

According to various embodiments, outputting the first sound signal may output the first sound signal if a strength of a sound signal received through the microphone 160 before outputting the first sound signal is less than a set value.

According to various embodiments, outputting the first sound signal may output the first sound signal after completing the output of the content sound signal if a content sound signal is being output through the speaker 150 before outputting the first sound signal.

According to various embodiments, each of the plurality of protocols may include information about frequencies of two pure tone signals, information about a frequency related to a distortion production otoacoustic emission of the two pure tone signals, information about strengths of the two pure tone signals, information about a strength of an anti-phase signal of a frequency related to the distortion production otoacoustic emission, and information about an angle of the anti-phase signal of the frequency related to the distortion production otoacoustic emission.

According to various embodiments, in at least some of the plurality of protocols, the strength of the anti-phase signal of the frequency related to the distortion production otoacoustic emission may be zero (0).

According to various embodiments, the method may further comprise performing calibration on the speaker 150 and the microphone 160 upon detecting a contact of the electronic device 100 to a cradle device corresponding to the electronic device 100.

According to various embodiments, the method may further comprise storing at least one of the changed sound volume or the changed equalization, transmitting the stored equalization to an external device 200 through a communication module of the electronic device 100, receiving a content sound signal to which the stored equalization is applied, from the external device 200, and outputting the received content sound signal through the speaker 150 based on the stored sound volume.

The electronic device 100, according to various embodiments of the disclosure, may be and/or include one of various types of electronic devices 100. The electronic devices 100 may include, for example, a portable communication device (e.g., a smartphone), a computer device, a portable multimedia device, a portable medical device, a camera, a wearable device, or a home appliance. According to an embodiment of the disclosure, the electronic devices 100 are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program) including one or more instructions that are stored in a storage medium (e.g., internal memory or external memory) that is readable by a machine (e.g., the electronic device 100). For example, a processor (e.g., the processor 120) of the machine (e.g., the electronic device 100) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program products may be traded as commodities between sellers and buyers. The computer program product may be distributed in the form of a machine-readable storage medium (e.g., compact disc read only memory (CD-ROM)), or be distributed (e.g., downloaded or uploaded) online via an application store (e.g., Play Store™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. Some of the plurality of entities may be separately disposed in different components. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

What is claimed is:

1. An electronic device, comprising:
a speaker;
a microphone;
a memory storing instructions and a plurality of protocols;
a digital signal processor (DSP);
a driver configured to convert a digital signal output from the DSP into an analog signal and output the analog signal to the speaker; and
a processor operatively coupled with the speaker, the microphone, the memory, the DSP, and the driver, wherein the processor is configured to execute the instructions to:
control the DSP to obtain a first sound signal by combining a first signal, a second signal, and a first anti-phase signal, based on a first protocol from among the plurality of protocols, the first anti-phase signal having a third frequency related to a distortion production otoacoustic emission (DPOAE) of a first frequency of the first signal and a second frequency of the second signal;
control the driver to output, through the speaker, the first sound signal;
receive, through the microphone, a second sound signal related to the first sound signal, in response to the output of the first sound signal;
extract, from the second sound signal, a first DPOAE signal of the third frequency;
control the DSP to obtain a third sound signal by combining a fourth signal, a fifth signal, and a second anti-phase signal, based on a second protocol among the plurality of protocols, the second anti-phase signal having a sixth frequency related to a DPOAE of a fourth frequency of the fourth signal and a fifth frequency of the fifth signal;
control the driver to output, through the speaker, the third sound signal;
receive, through the microphone, a fourth sound signal related to the third sound signal, in response to the output of the third sound signal;
extract, from the fourth sound signal, a second DPOAE signal of the sixth frequency;
obtain a user hearing profile based on the first DPOAE signal and the second DPOAE signal; and
perform, based on the user hearing profile, at least one of a sound volume change and an equalization (EQ) change of a sound to be output.

2. The electronic device of claim 1, wherein the processor is further configured to execute further instructions to:
compute, based on the user hearing profile, a strength difference between a plurality of frequencies comprised in the sound to be output;
determine whether the strength difference is within a set range; and
based on a determination that the strength difference is outside the set range, change, based on the user hearing profile, the EQ of the sound to be output so that another strength difference of the sound to be output is within the set range.

3. The electronic device of claim 1, wherein the processor is further configured to execute further instructions to:
provide feedback indicating that hearing of a user is deteriorated, based on the user hearing profile.

4. The electronic device of claim 1, wherein the processor is further configured to execute further instructions to:
based on a strength of a sound signal received through the microphone before outputting the first sound signal being less than a set value, output the first sound signal.

5. The electronic device of claim 1, wherein the processor is further configured to execute further instructions to:
based on a content sound signal being output through the speaker before outputting the first sound signal, output the first sound signal after completing the output of the content sound signal.

6. The electronic device of claim 1, wherein the processor is further configured to execute further instructions to:
output the first sound signal based on a set period.

7. The electronic device of claim 1, wherein each protocol of the plurality of protocols comprises:
information about frequencies of two pure tone signals,
information about a frequency related to a DPOAE of the two pure tone signals,
information about strengths of the two pure tone signals,
information about a strength of an anti-phase signal of the frequency related to the DPOAE, and
information about a phase of the anti-phase signal of the frequency related to the DPOAE.

8. The electronic device of claim 7, wherein at least one of the plurality of protocols has a strength of the anti-phase signal of the frequency related to the DPOAE set to zero (0).

9. The electronic device of claim 1, further comprising:
an ear probe to be inserted into an outer ear of a user,
wherein the speaker and the microphone are disposed on a portion of the ear probe.

10. The electronic device of claim 1, wherein the processor is further configured to execute further instructions to:
perform calibration on the speaker and the microphone in response to detecting a contact of the electronic device to a cradle device corresponding to the electronic device.

11. The electronic device of claim 1, further comprising:
a communication module,
wherein the processor is further configured to execute further instructions to:
store, in the memory, at least one of the changed sound volume and the changed EQ;
transmit, through the communication module to an external device, the stored EQ;
receive, from the external device, a content sound signal to which the stored EQ is applied; and
control the driver to output, through the speaker, the received content sound signal based on the stored sound volume.

12. A method for controlling an electronic device, comprising:

outputting, through a speaker of the electronic device, a first sound signal obtained by combining a first signal having a first frequency, a second signal having a second frequency, and a first anti-phase signal having a third frequency related to a distortion production otoacoustic emission (DPOAE) of the first frequency and the second frequency, based on a first protocol from among a plurality of protocols stored in a memory of the electronic device;

in response to receiving, through a microphone of the electronic device, a second sound signal related to the first sound signal, extracting, from the second sound signal, a first DPOAE signal of the third frequency;

outputting, through the speaker, a third sound signal obtained by combining a fourth signal having a fourth frequency, a fifth signal having a fifth frequency, and a second anti-phase signal having a sixth frequency related to a DPOAE of the fourth frequency and the fifth frequency, based on a second protocol from among the plurality of protocols;

in response to receiving, through the microphone, a fourth sound signal related to the third sound signal extracting, from the fourth sound signal, a second DPOAE signal of the sixth frequency;

obtaining a user hearing profile based on the first DPOAE signal and the second DPOAE signal; and performing, based on the user hearing profile, at least one of a sound volume change and an equalization (EQ) change of a sound to be output.

13. The method of claim 12, wherein the performing of the at least one of the sound volume change and the equalization (EQ) change comprises:

based on determining that a strength difference between a plurality of frequencies comprised in the sound to be output is outside of a set range, changing, based on the user hearing profile, the EQ of the sound to be output so that another strength difference of the sound to be output is within the set range.

14. The method of claim 12, further comprising:

providing feedback indicating that hearing of a user is deteriorated, based on the user hearing profile.

15. The method of claim 12, wherein the outputting of the first sound signal comprises:

outputting the first sound signal based on a strength of a sound signal received through the microphone before outputting the first sound signal being less than a set value.

16. The method of claim 12, wherein the outputting of the first sound signal comprises:

based on a content sound signal being output through the speaker before outputting the first sound signal, outputting the first sound signal after completing the outputting of the content sound signal.

17. The method of claim 12, wherein the outputting of the first sound signal comprises:

outputting the first sound signal based on a set period.

18. The method of claim 12, wherein each protocol of the plurality of protocols comprises:

information about frequencies of two pure tone signals, information about a frequency related to a DPOAE of the two pure tone signals, information about strengths of the two pure tone signals, information about a strength of an anti-phase signal of the frequency related to the DPOAE, and information about a phase of the anti-phase signal of the frequency related to the DPOAE.

19. The method of claim 12, further comprising:

performing calibration on the speaker and the microphone in response to detecting a contact of the electronic device to a cradle device corresponding to the electronic device.

20. An electronic device, comprising:

a memory storing instructions and a plurality of protocols;

a processor operatively coupled with the memory, wherein the processor is configured to execute the instructions to:

obtain a plurality of related sound signals by combining, according to respective protocols of the plurality of protocols, a plurality of first signals, a plurality of second signals, and a plurality of anti-phase signals having third frequencies related to distortion production otoacoustic emissions (DPOAEs) of first frequencies of the plurality of first signals and second frequencies of the plurality of second signals;

transmit the plurality of related sound signals;

receive, based on the transmitted plurality of related sound signals, a corresponding plurality of received sound signals;

extract a plurality of DPOAE signals from the corresponding plurality of received sound signals;

obtain a user hearing profile based on the plurality of DPOAE signals; and perform, based on the user hearing profile, at least one of a sound volume change and an equalization (EQ) change of a sound to be output.

*   *   *   *   *